United States Patent [19]

Muchowski et al.

[11] 3,935,241

[45] Jan. 27, 1976

[54] 11α-METHYLSUBSTITUTED PROSTAGLANDIN DERIVATIVES

[75] Inventors: Joseph M. Muchowski; Angel Guzman, both of Mexico City, Mexico

[73] Assignee: Syntex (U.S.A.) Inc., Palo Alto, Calif.

[22] Filed: May 10, 1974

[21] Appl. No.: 468,772

[52] U.S. Cl.......... 260/468 D; 260/349; 260/488 R; 260/514 D; 424/305; 424/317

[51] Int. Cl.²............. C07C 147/02; C07C 147/14; C07C 149/26

[58] Field of Search............ 260/349, 468 D, 514 D

[56] References Cited
UNITED STATES PATENTS
3,845,042  10/1974  Stnk et al.............................. 260/24

OTHER PUBLICATIONS

Fieser et al., Reagents, For Organic Synthesis, p. 810, 1247, 1248, (1967).

Fieser et al., Reagents for Organic Synthesis, Vol. 3, p. 36, (1972).

Wygand et al., Preparative organic Chemistry, p. 638, (1971).

*Primary Examiner*—Robert Gerstl
*Attorney, Agent, or Firm*—Gerard A. Blaufarb; William B. Walker

[57] ABSTRACT

Novel 8R-antimeric and racemic 11α-methylsubstituted-prosta-5-cis, 13-trans-dienoic and prost-13-trans-enoic acids having oxygenated functions at the C-9 and C-15 positions of the molecule, as well as the 15-methyl or ethyl derivatives thereof and processes for making such compounds. Also encompassed are the pharmaceutically acceptable, non-toxic alkyl esters and salts of the carboxylic acid function of these novel compounds.

7 Claims, No Drawings

11α-METHYLSUBSTITUTED PROSTAGLANDIN DERIVATIVES

The present invention relates to certain novel prostaglandin derivatives and to processes for the production thereof.

More particularly the present invention relates to natural and racemic prosta-5-cis,13-trans-dienoic acids and prost-13-trans-enoic acids having oxygenated functions at C-9 and C-15 positions of the molecule and a methyl substituted group at C-11, as well as the 15-methyl or ethyl derivatives thereof. Also encompassed are the corresponding pharmaceutically acceptable, non-toxic alkyl esters and salts of the carboxylic acid function.

Prostaglandins are members of a relatively new class of hormonal agents with a remarkable range of biological and pharmaceutical properties. These compounds belong to a group of chemically related 20-carbon chain hydroxy fatty acids having the basic skeleton of prostanoic acid:

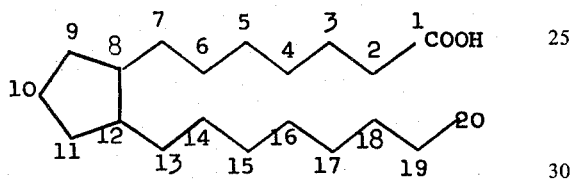

For a review on prostaglandins and the definition of primary prostaglandins, see for example S. Bergström, *Recent Progress in Hormone Research*, 22, pp. 153–175 (1966) and *Science*, 157, page 382 (1967) by the same author.

Prostaglandins are widely distributed in mammalian tissues and have been isolated from natural sources in very small amounts. In addition, a number of the naturally occurring prostaglandins have been prepared by chemical synthesis, note for example, E. J. Corey et al., *J. Am. Chem. Soc.*, 91, page 5675 (1969), *J. Am. Chem. Soc.* 92, page 2586 (1970) and *J. Am. Chem. Soc.*, 93, pages 1489–1493 (1971) and references cited therein, W. P. Schneider et al., *J. Am. Chem. Soc.*, 90, page 5895 (1968), U. Axen et al, *Chem. Commun.*, page 303 (1969) and W. P. Schneider, *Chem. Commun.*, page 304, (1969).

It has also been reported by A. J. Weinheimer et al, [*Tetrahedron Letters*, 5183 (1969)] that a type of coral, the sea whip or sea fan *Plexaura homomalla* found in reefs off the Florida coast, in the Caribbean region, contains high concentrations of prostaglandin derivatives of the $PGA_2$ series, to which they assigned the unnatural (R) configuration for the hydroxyl group at C-15. More recently, W. P. Schneider et al, [*J. Am. Chem. Soc.*, 94, 2122 (1972)] reported that some forms of *P. homomalla* contain, instead of the (15R)-prostaglandins, free or esterified derivatives of (15S)-$PGA_2$, identical with the prostaglandins derived from mammalian sources. They also found that some specimens of this gorgonian may contain both (15R) and (15S) prostaglandins.

Because of the remarkable range of biological and pharmacological properties exhibited by this family of compounds, a great deal of interest has focused upon such compounds, and the preparation of analogs of such compounds; accordingly, we have discovered certain modified novel prostaglandin derivatives and processes for the production thereof.

The novel prostaglandin derivatives of the present invention can be represented by the following formulas:

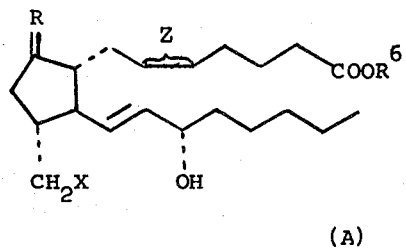

(A)

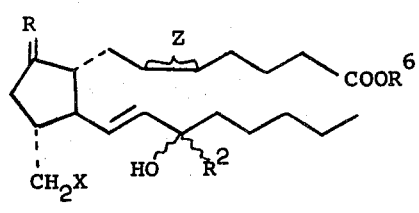

(B)

wherein

R is a keto group, α-hydroxy-β-hydrogen or β-hydroxy-α-hydrogen;

X is fluoro, chloro, bromo, azido ($N_3$), amino (—$NH_2$), mono or disubstituted amino (—$NR^4R^5$), formamido (—NHCHO), lower alkylamido (—$NHCOR^3$), lower alkoxy, thiomethyl, methylsulfinyl

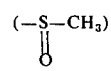

or methylsulfonyl

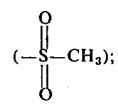

$R^2$ is methyl or ethyl;

each of $R^3$ and $R^4$ is independently a lower alkyl group containing from 1 to 4 carbon atoms;

$R^5$ is hydrogen or a lower alkyl group containing from 1 to 4 carbon atoms;

$R^6$ is hydrogen, a lower alkyl group of 1 to 4 carbon atoms or the pharmaceutically acceptable, non-toxic salts of compounds in which $R^6$ is hydrogen;

Z is a saturated linkage or a cis double bond and the wavy lines ( ) indicate the α or 6ξ configuration or mixtures thereof, provided that when $R^2$ is α, the hydroxyl group, attached to the same carbon atom as $R^2$, is β; and when $R^2$ is β, the hydroxyl group, attached to the same carbon atoms as $R^2$ is α.

The dotted lines shown in the above formula and in the formulas below indicate that the substituents are in α configuration, i.e., below the plane of the cyclopentane ring.

The double bonds in the compounds of the present invention have the same configuration as in natural prostaglandins of the $PGE_1$, $PGE_2$, $PGF_{1\alpha}$ and $PGF_{2\alpha}$ series, i.e., the double bond at C-5,6 is in cis-configuration and the double bond at C-13,14 is in trans-configuration.

These novel compounds possess asymmetric centers and thus can be produced as racemic mixtures. The racemic mixtures can be resolved if desired, at appropriate stages by methods known to those skilled in the art, to obtain the respective individual antimers. It is to be understood that the individual antimers as well as mixtures of both antimers are encompassed within the scope of the present invention. The preferred antimeric compounds are the 8R-antimers, i.e., the optically active forms corresponding to prostaglandins obtained from natural sources.

When the compounds of the present invention are racemic mixtures, they are produced starting from racemates, while when the compounds of the invention are individual antimers, they are preferably obtained starting from the appropriate individual antimer.

For the sake of simplicity only one antimer of each pair will be depicted in the description of the process and claims; however, it is to be understood that the mirror images for the racemic mixtures and the individual antimers are also encompassed thereby.

The use of the symbol "R" preceding a substituent designates the absolute stereochemistry of that substituent according to the Cahn-Ingold-Prelog rules [see Cahn et al., *Angew. Chem. Inter. Edit.*, Vol. 5, p. 385 (1966), errata p. 511; Cahn et al., *Angew. Chem.*, Vol. 78, p. 413 (1966); Cahn and Ingold, *J. Chem. Soc.*, (London), 1951, p. 612; Cahn et al., *Experientia*, Vol. 12, p. 81 (1956); Cahn., *J. Chem. Educ.*, Vol. 41, p. 116 (1964)]. Because of the interrelation of the designated substituent with the other substituents in the compound having α or β prefixes, the designation of the absolute configuration of one substituent fixes the absolute configuration of all substituents in the compound and thus the absolute configuration of the compound as a whole.

The term "lower alkyl" as used herein refers to straight or branched alkyl groups containing up to 4 carbon atoms, e.g., methyl, ethyl, n-propyl, isopropyl, n-butyl, t-butyl and the like.

The term "lower alkoxy" refers to the group $R^1O-$ wherein $R^1$ is lower alkyl. Typical lower alkoxy groups include, for example, methoxy, ethoxy, propoxy, isopropoxy, t-butoxy and the like.

The term "substituted amino" refers to mono (lower) alkyl- and di (lower) alkylamino groups in which "lower alkyl" is as defined above. Typical mono (lower) alkyl amino groups included within the scope of the instant invention are: methylamino, ethylamino, n-propylamino, isopropylamino, n-butylamino, t-butylamino and the like.

Examples of di(lower)alkylamino groups included within the scope of the present invention are: dimethylamino, diethylamino, ethylmethylamino, di-n-propylamino, methyl-n-propylamino, di-n-butylamino, di-t-butylamino, methyl-t-butylamino and the like.

The term "lower alkylamido" refers to lower alkylcarbonylamino groups in which "lower alkyl" is as defined above, such as acetamido, n-propionamido, isopropionamido, butyramido, etc.

The term "conventionally hydrolyzable esters" refers to those physiologically acceptable lower alkyl ester groups employed in the pharmaceutical art, particularly the methyl, ethyl and propyl esters.

The addition salts of the compounds of the present invention are derived from pharmaceutically acceptable basic salts, including metal salts such as sodium, potassium, calcium, magnesium, aluminum and the like, as well as organic amine salts such as ammonium., triethylamine, 2-dimethylaminoethanol, 2-diethylaminoethanol, lysine, arginine, caffeine, procaine, N-ethylpiperidine, and the like.

The novel compounds of the present invention can be obtained by the following overall reaction sequence:

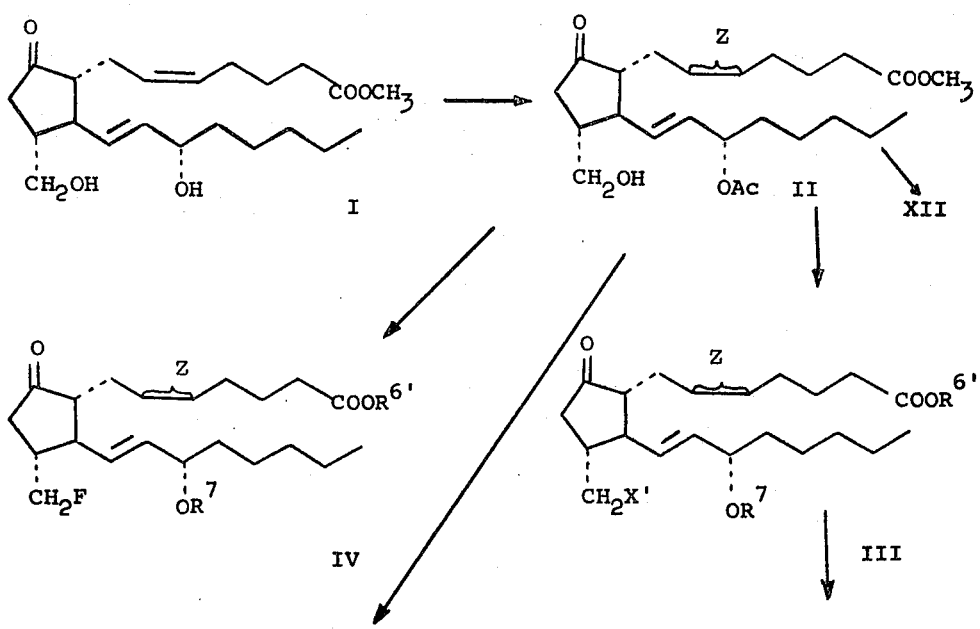

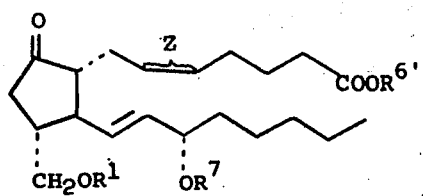
V
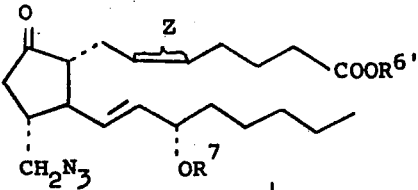
VI
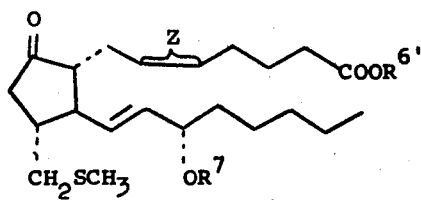
IX
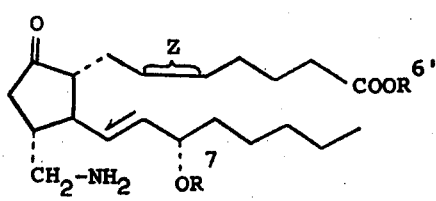
VII
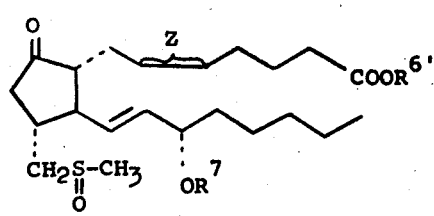
X
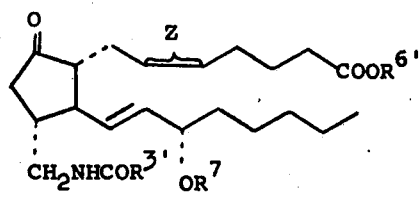
VIII
X
II
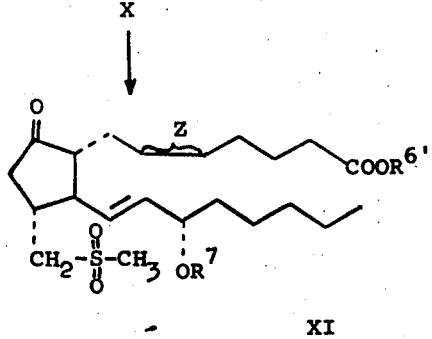
XI
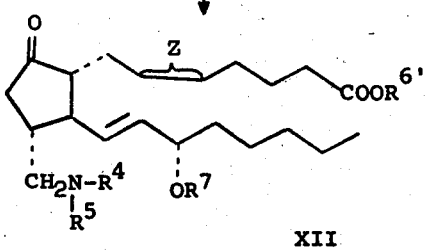
XII
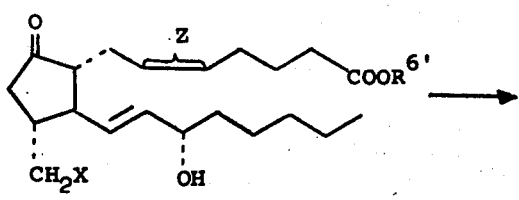
XIII
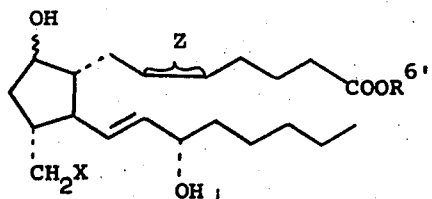
XIV

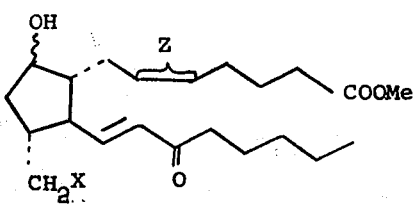

XV

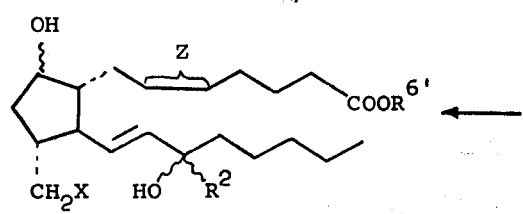

XVI

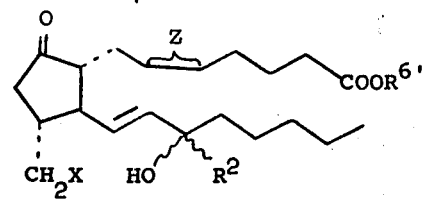

XVII wherein
Z, $R^1$, $R^2$, $R^4$ and $R^5$ have the above-indicated meaning;
$R^{3'}$ is hydrogen or lower alkyl;
$R^{6'}$ is hydrogen or methyl;
$R^7$ is hydrogen or acetyl (Ac) and
X' is chloro or bromo.

In practicing the process illustrated above the starting materials, 8R-9-keto-11α-hydroxymethyl-15α-hydroxyprosta-5-cis,13-trans-dienoic acid methyl ester or its racemate, compounds of the formula I, are treated with acetic anhydride in pyridine solution, in a conventional manner, to produce the diacetylated derivative, in which the acetoxymethyl group at C-11 is selectively hydrolyzed, to yield the 15-monoacetate of formula II (Z = double bond). This selective saponification is effected using about 1.1 molar equivalents of an anhydrous alkali metal carbonate such as sodium carbonate or potassium carbonate in an anhydrous aliphatic alcohol as solvent, i.e. methanol or ethanol at about room temperature or below, for a period of time of the order of 1 to 4 hours, 2 hours being generally sufficient.

The compounds of formula II (Z = saturated linkage) are obained by selective reduction of the C-5,6 double bond in the diene compounds (II, Z = double bond). This selective reduction can be effected by the procedure described by Koch et al., in *Journal of Labelled Compounds*, Vol. VI, No. 4, page 395 (October-December 1970) using tris (triphenylphosphine) chlororhodium as catalyst, in a suitable inert organic solvent or mixture of solvents, such as a benzene-acetone mixture, at about room temperature, or using platinum oxide or a palladium-charcoal catalyst in a lower aliphatic alcohol as solvent, i.e., in methanol or ethanol solution at a temperature comprised between −20°C to room temperature, until absorption of about one molar equivalent of hydrogen, using in both cases a thin layer chromatographic analytical technique to follow the progress of the reaction.

By treatment of compounds of formula II with a trisubstituted phosphine dichloride or dibromide, under appropriate conditions, there are obtained the corresponding chloromethyl or bromomethyl compounds of formula III ($R^{6'}$ = Me; $R^7$ = Ac).

The phosphine dihalide reagents are obtained from trisubstituted phosphines such as triphenyl phosphine, tri-n-octylphosphine, tris(dimethylamino) phosphine and the like, in the presence of a chlorine or bromine source.

In the preferred embodiments, this reaction is effected by using triphenylphosphine dichloride or dibromide in a suitable inert organic solvent. Typically, this reaction is effected by first saturating a solution of triphenylphosphine in an anhydrous inert organic solvent, e.g. dimethoxyethane, dimethylformamide, dimethylacetamide and the like with gaseous chlorine, or bromine, at room temperature, and thereafter cooling the triphenylphosphine dihalide reagent thus obtained to 0°C and adding a solution of compound of formula II in the same solvent. There are used from 1 to 2 molar equivalents of triphenylphosphine per molar equivalent of compound of formula II, and preferably about 1.5 molar equivalents. The reaction mixture is then maintained at about 0°C for a short period of time of the order of 10 to 40 minutes, preferably for about 30 minutes. Upon evaporation of the solvent and purification of the residue by thin-layer chromatography there is obtained the corresponding 11α-halomethyl compound of formula III ($R^{6'}$ = Me; $R^7$ = Ac).

Alternatively, the 11α-chloromethyl and 11α-bromomethyl compounds of formula III ($R^{6'}$ = Me; $R^7$ = Ac) can be prepared by reaction of compounds of formula II with at least one molar equivalent of triphenylphosphine and carbon tetrachloride or carbon tetrabromide as halogen source, in accordance with the method of J. B. Lee et al., *Tetrahedron* 23, 2789 (1967) or with tri-n-octylphosphine-carbon tetrachloride or carbon tetrabromide, in accordance with the method of J. Hooz et al, *Canadian J. Chem.* 46, 86 (1968). In both cases, carbon tetrachloride and carbon tetrabromide can serve both as reagents and solvents. This reaction can also be effected in an inert organic solvent e.g., dimethylformamide, dimethoxyethane, diethyl ether and the like, using only about 1 to 5 molar equivalents of the carbon tetrahalide. In any case the reaction can be conducted at a temperature comprised between room temperature and reflux, for a period of time of the order of from about 10 minutes to several hours.

In a further aspect, the 11α-chloromethyl and 11α-bromomethyl compounds of formula III can also be prepared by treatment of compounds of formula II with tris(dimethylamino)phosphine and carbon tetrachloride or carbon tetrabromide respectively, followed by treatment of the alkyloxytris(dimethylamino)phosphonium halide intermediate with lithium chloride or bromide, in accordance with the method of B. Castro et al., *Bull. Soc. Chimique de France*, 1973 p. 3034. In the preferred embodiments the reaction is conducted by adding from about 1.6 to 2 molar equivalents of tris(dimethylamino) phosphine to a solution of the compound of formula II in an inert organic solvent, e.g., dimethylformamide or pyridine containing at least 2 molar equivalents of carbon tetrachloride or carbon tetrabromide, at low temperature, of the order of 0° to −70°C, preferably at about −40° to −45°C, following the course of the reaction by thin layer chromatographic analytical techniques; when the reaction is essentially complete there are added from 1 to 1.2 molar equivalents of lithium chloride (when carbon tetrachloride has been used) or lithium tetrabromide in the case of using previously carbon tetrabromide, heating the mixture at about 80° to 120°C for a prolonged period of time, of the order of 20 to 40 hours; good results are obtained conducting the reaction at about 110°C for about 24 hours. This method is also applicable to starting materials having a free hydroxyl group at C-15, thus producing directly the 11α-halomethyl compounds of formula III in which $R^{6'}$ = Me; $R^7$ = H.

The 11α-fluoromethyl compounds of formula IV ($R^{6'}$ = Me; $R^7$ = Ac) can be prepared from the corresponding 11α-hydroxymethyl compounds of formula II by a four step sequence, which comprises protection of the 9-keto group as the diethyleneketal, treatment of the ketal with methyltriphenoxyphosphonium iodide in accordance with the method of J. P. H. Verheyden et al., *J. Org. Chem.*, 35, 2319 (1970) to produce the 11α-iodomethyl prostaglandin derivative, displacement of the iodine atom by fluorine by reaction with silver fluoride and hydrolysis of the ketal protecting group by acid treatment.

Typically, the ketalization of the 9-keto function is effected by treatment of compound of formula II with 2-methyl-2-ethyl-1,3-dioxolane in the presence of an acid catalyst, e.g., p-toluenesulfonic acid, at the boiling point with continuous distillation, for about 1 hour. The product is isolated from the reaction mixture by dilution with water, extraction with a solvent immiscible with water, e.g., diethyl ether, methylene chloride, ethyl acetate and the like, evaporation and purification by thin layer chromatography.

The reaction with methyltriphenoxyphosphonium iodide is effected using about 2 molar equivalents of this reagent (prepared as described by J. P. H. Verheyden et al., vide supra) per molar equivalent of compound II in an inert organic solvent, using particularly dimethylformamide as solvent, at room temperature for a short period of time, of the order of 10 to 30 minutes, the excess reagent being destroyed by addition of methanol when the reaction is essentially complete, isolating the product by extraction with a solvent immiscible with water, evaporation and purification by thin layer chromatography.

The displacement of iodine by fluorine is carried out using an excess of silver fluoride in aqueous acetonitrile, under slight heating, i.e., at about 30° to 40°C, for a period of time of the order of 4 to 10 hours. Upon acid hydrolysis of the ethylenedioxy protecting group, using for example aqueous acetic acid (24 hours at room temperature) or p-toluenesulfonic acid in acetone solution (3 hours at room temperature), there is obtained the desired 9-keto-11α-fluoromethyl compound of formula III ($R^{6'}$ = Me; $R^7$ = Ac).

The 11α-iodomethyl intermediate can be alternatively obtained by treatment of the 9-ethylenedioxy-11α-hydroxymethyl compound with triphenylphosphine or tri-n-octylphosphine-carbon tetrabromide, as described hereinbefore in detail, followed by displacement of bromine by iodine, by treatment with sodium iodide in acetone.

Upon treatment of compounds of formula II with an alkyl iodide such as methyl iodide, ethyl iodide, isopropyl iodide and the like in the presence of an alkali metal hydride, e.g., sodium hydride, in an anhydrous inert organic solvent there are produced the corresponding 11α-alkoxymethyl compounds of formula V ($R^{6'}$ = Me; $R^7$ = Ac). The reaction is preferably conducted under nitrogen or argon atmosphere, at room temperature for a prolonged period of time, of the order of 16 to 30 hours. Suitable inert organic solvents are dimethylformamide, dimethylacetamide, tetrahydrofuran, dimethylsulfoxide, etc.

The 11α-azidomethyl compounds of formula VI ($R^{6'}$ = Me; $R^7$ = Ac) are prepared by treatment of the 11α-bromomethyl compounds of formula III ($R^{6'}$ = Me; $R^7$ = Ac; $X'$ = Br) with an excess of sodium azide in an aqueous inert organic solvent. In the preferred embodiments, there are used from 6 to 25 molar equivalents of sodium azide per molar equivalent of starting compound III in a solvent miscible with water, e.g., acetone and dimethylsulfoxide in the presence of about 10–15% water, conducting the reaction at a temperature comprised between room temperature and reflux, for a period of time of the order of 12 to 48 hours, the reaction time depending upon the temperature at which the reaction takes place.

The 11α-aminomethyl compounds of formula VII ($R^{6'}$ and $R^7$ = H) can be obtained by reaction of the corresponding 11α-azidomethyl compounds of formula VI ($R^{6'}$ = Me; $R^7$ = Ac) with triphenylphosphine in an anhydrous inert organic solvent followed by base treatment of the aminophosphorane intermediate so produced, with concomitant hydrolysis of the protecting groups at C-1 and C-15.

Typically, there is used from 1 to 1.2 molar equivalents of triphenylphosphine per molar equivalent of the azidomethyl starting compound of formula VI. Adequate inert organic solvents for this reaction are benzene, toluene, acetonitrile and the like, conducting the reaction at a temperature comprised between room temperature and reflux, for a period of time of the order of 2 to several hours. In the preferred embodiments, the reaction is initially maintained at room temperature for about 2 hours, and thereafter heated under refluxing conditions until it is essentially complete, as demonstrated by thin layer chromatographic analysis. The solvent is eliminated under reduced pressure and the residue treated with a dilute solution of an alkali metal hydroxide, i.e., sodium or potassium hydroxide in a lower aliphatic alcohol, e.g., methanol or ethanol, at reflux temperature for about 2 to 5 hours, preferably for about 3 hours under nitrogen or argon atmosphere, followed by evaporation of the solvent, disolution of the residue in water and filtration of the aqueous solution through a column of a strongly acidic cation exchange resin (in H+ form) such as Amberlite or Dowex 50, acid form (+) eluting the column first with water and thereafter with dilute acetic acid, e.g., 10% aqueous acetic acid. The acidic eluates are evaporated, lyophilized and purified by chromatographic techniques, to afford the 11α-aminomethyl prostaglandin derivatives of formula VII ($R^{6'}$ and $R^7$ = H).

Upon conventional acetylation of the 15α-hydroxy group with acetic anhydride in pyridine solution, 1 hour at room temperature and esterification of the carboxylic acid function with etheral diazomethane there are produced the diesterified compounds (VII, $R^{6'}$ = Me; $R^7$ = Ac), which can be further purified by thin layer chromatography.

By treatment of the 11α-aminomethyl compounds of formula VII ($R^{6'}$ = Me; $R^7$ = Ac) with a carboxylic acid anhydride or carboxylic acid chloride of 2 to 5 carbon atoms in pyridine solution, at room temperature for a period of time of about 12 to 20 hours there are produced the alkylamidomethyl derivatives of formula VIII ($R^{3'}$ = lower alkyl, $R^{6'}$ = Me; $R^7$ = Ac). This reaction can also be effected at the steambath temperature for 1 to 3 hours.

The 11α-formamidomethyl compounds (VIII, $R^{3'}$ = H; $R^{6'}$ = Me; $R^7$ = Ac) can be prepared by reaction of the corresponding 11α-aminomethyl compounds (VII, $R^{6'}$ = Me; $R^7$ = Ac) with phenyl formate, in an inert organic solvent. Typically, the reaction is conducted by adding a cold solution of the 11α-aminomethyl starting compound in an inert organic solvent such as diethyl ether, isopropyl ether, tetrahydrofuran, dioxane and the like, to a slight excess of phenyl formate (i.e., from 1.1 to 1.5 molar equivalents), maintaining the reaction mixture at a temperature of between 0°C to room temperature for about 12 to 24 hours. The phenyl formate used as reagent can be in pure form or contaminated with phenol and other impurities, which do not interfere with the reaction. Thus, there can be used phenyl formate prepared as described by H. L. Yale in *J. Org. Chem.* 36, 3238 (1971) which contains approximately 50% of phenyl formate, 45% phenol and 5% unidentified products. When the reaction is complete, the product is isolated from the reaction mixture by evaporation of the solvent and excess reagent under high vacuo, dissolving the residue in a solvent immiscible with water followed by washing with water or sodium chloride solution to eliminate the phenol and other impurities, evaporation and chromatographic purification.

The 11α-methylthiomethyl compounds of formula IX ($R^{6'}$ = Me; $R^7$ = Ac) can be prepared by treatment of the corresponding 11α-bromomethyl compounds of formula III ($R^{6'}$ = Me; $R^7$ = Ac; $X'$ = Br) with sodium thiomethylate in anhydrous methanol. The reaction is preferably conducted under an inert atmosphere, i.e., under argon or nitrogen atmosphere, at a temperature comprised between 0°C to room temperature for a period of time of about 2 to 48 hours, using at least 1.1 molar equivalents of sodium thiomethylate per molar equivalent of starting compound. In general, the reaction is complete within about 6 hours, at room temperature.

Upon treatment of the 11α-methylthiomethyl compounds formula IX ($R^{6'}$ = Me; $R^7$ = Ac) with sodium metaperiodate, at low temperature, there are produced the 11α-methylsulfinylmethyl derivatives of formula X($R^{6'}$ = Me; $R^7$ = Ac). This oxidation reaction is conveniently carried out by addition of a solution of the 11α-methylthiomethyl starting compound (IX) in a lower aliphatic alcohol e.g., methanol or ethanol to a slight molar excess of sodium metaperiodate (in the form of a 0.5M aqueous solution), at a temperature of about 0°C for a period of time of about 3 to 24 hours. The precipitated sodium iodide is removed by filtration, and the product isolated from the filtrate by conventional techniques.

By reaction of the 11α-methylsulfinylmethyl compounds of formula X ($R^{6'}$ = Me; $R^7$ = Ac) with N-chlorosuccinimide or N-bromosuccinimide in anhydrous methanol there are produced the corresponding 11α-methylsulfonylmethyl derivatives of formula XI ($R^{6'}$ = Me; $R^7$ = Ac). Typical conditions involve the use of from 1 to 2 equivalents of the N-halosuccinimide reagent per molar equivalent of compound of formula X, using a large volume of methanol. The reaction is conducted at a temperature comprised between 0°C to room temperature, for about 1 to several hours. In the preferred embodiments 1.1 to 1.2 molar equivalents of the N-halosuccinimide reagent are added to a dilute methanolic solution of the 11α-methylsulfinylmethyl starting compound, cooled to 0°C, maintaining the reaction mixture at room temperature until the reaction is complete, usually for about 1 to 2 hours. The product is isolated from the reaction mixture by conventional means, such as evaporation of the methanol, disolution of the residue in a solvent immiscible with water, e.g., methylene chloride, diethyl ether, ethyl acetate and the like, washing the organic solution with water or brine to eliminate the succinimide formed during the reaction, evaporation and thin layer chromatographic purification.

The 11α-N-(lower)-alkylaminomethyl and N,N-di(-lower)alkylaminomethyl compounds of formula XII ($R^{6'}$ = Me; $R^7$ = Ac) can be prepared from the corresponding 11α-hydroxymethyl compounds of formula II, by treatment with tris(dimethylamino)phosphine, carbon tetrachloride and ammonium perchlorate in a suitable inert solvent, to give a methyloxydimethylaminophosphonium perchlorate intermediate which is immediately treated with a lower alkyl- or lower dialkylamine, to yield the corresponding 11α-N-alkylaminomethyl or 11α-N,N-dialkylaminomethyl derivative of formula XII ($R^{6'}$ = Me; $R^7$ = Ac).

Typically, to a solution of the starting compound of formula II in a mixture of carbon tetrachloride and an anhydrous inert organic solvent, e.g., dimethylformamide, acetonitrile, methyl ethyl ketone, hexamethylphosphotriamide and the like, particularly dimethylformamide, cooled to a temperature comprised between —40° to —78°C, preferably to about —60°C is slowly added one equivalent of tris(dimethylamino)phosphine, under an inert atmosphere, i.e., under argon or nitrogen atmosphere, and thereafter a solution of about one equivalent of ammonium perchlorate in the same solvent previously used. A precipitate of ammonium chloride is readily formed, remaining in solution the methyloxydimethylaminophosphonium perchlorate prostaglandin intermediate, which is immediately treated with at least two molar equivalents of a mono(lower)alkyl or di(lower)alkylamine, heating the mixture at a temperature comprised between 60° to 130°C for a period of time of the order of 3 to 48 hours, preferably at 80°C for about 10 hours. The product is isolated from the reaction mixture by conventional techniques such as dilution with water, extraction, evaporation and chromatographic purification.

Suitable mono(lower)alkyl amines used in this reaction are methylamine, ethylamine, n-propylamine, isopropylamine, n-butylamine, t-butylamine, etc. Suitable di(lower)alkylamines are: dimethylamine, diethylamine, methylethylamine, di-n-propylamine, di-isopropylamine, di-n-butylamine, methylethylamine, methylisobutylamine, methyl-n-propylamine and the like.

The 15α-acetoxy function in compounds of formulas III to XII ($R^{6'}$ =Me; $R^7$ = Ac) can be selectively hydrolyzed by chemical or enzymatic methods, to yield the respective 15α-hydroxy compounds (III to XII, $R^{6'}$ = Me; $R^7$ = H).

The acetoxy function in the 11α-halomethyl compounds of formulas III and IV is preferably hydrolyzed by enzymatic methods using an aged endogenous enzyme system present in the cortex of Plexaura homomalla (Esper), in accordance with the method described by A. Prince et al., in *Prostaglandins* Vol. 3, No. 4, p. 531 (1973). This method comprises putting into contact a suspension of 1 part of the methyl ester15-acetoxy-prostaglandin used as substrate and from 5 to 20 parts by weight of aged extracted, finely ground gorgonian, in a saline solution containing sodium chloride and calcium chloride, stirring the mixture at about room temperature for about 24 hours, following the course of the reaction by t.l.c. analysis. Dilution of the reaction mixture with acetone, separation of the insoluble material by filtration or decantation, evaporation of the acetone, extraction of the aqueous layer with a solvent immiscible with water, evaporation of the organic extract and purification of the residue by chromatography on silica gel plates affords the desired methyl ester-15α-hydroxy-prostanoic acid derivative (III and IV, $R^{6'}$ =Me; $R^7$= H).

Alternatively, this selective enzymatic hydrolysis can be carried out by using citrus acetyl esterase [see for example J. D. A. Jeffery et al, *Biochem. J.* 81, p. 591 (1961) and U.S. Pat. No. 3,769,166].

When using a recently extracted residue of the gorgonian Plexaura homomalla (Esper) in the above mentioned method, conducting the reaction at a pH 7.5-7.7, both the acetoxy and methyl ester groups are hydrolyzed, thus giving rise to the free 11α-halomethyl-15α-hydroxy prostadienoic or prostenoic acids (III and IV, $R^{6'}$ and $R^7$ = H).

The acetoxy function in compounds of formulas V to XII can be hydrolyzed by the above mentioned enzymatic methods, or by treatment with about 1 to 1.5 equivalents of an anhydrous alkali metal carbonate such as sodium carbonate or potassium carbonate in methanol solution under anhydrous conditions, at about room temperature or below for a period of time of the order of 1 to 3 hours, preferably conducting the reaction under nitrogen or argon atmosphere.

Compounds of formulas V, VI, VIII, IX, X and XI ($R^{6'}$ = Me; $R^7$ = Ac) can be converted into the corresponding 15-hydroxy prostadienoic and prostenoic acids (V, VI, VIII, IX, X and XI, $R^{6'}$ and $R^7$ = H) by treatment with an excess of an alkali metal carbonate or alkali metal hydroxide in aqueous methanol, at room temperature or under slight heating, i.e., at a temperature of the order of 20° to 40°C for a period of time of about 12 to 24 hours, under an inert atmosphere.

Alternatively, the hydrolysis of the methyl ester group can be effected by enzymatic hydrolysis methods, using for example a crude pancreatic lipase commercially available (Sigma Steapsin), or a crude hog pancreatic lipase, by the method of A. F. Kluge et al in *J. Am. Chem. Soc.* 94, 782 (1972), baker's yeast [C. J. Sih et al, *J. C. S. Chem. Comm.* 240 (1972)] or a recently extracted residue of the gorgonian Plexaura homomalla (Esper).

The methyl esters of 8R-antimeric and racemic 9-keto-11α-methylsubstituted-15α-hydroxyprostenoic and prostadienoic acid compounds (formula XIII, $R^{6'}$ = Me, which is a composite of formulas III to XII, $R^{6'}$ = Me; $R^7$= H) are converted into the 9-hydroxy derivatives of formula XIV ($R^{6'}$ = Me) by reduction with sodium borohydride or zinc borohydride.

The reduction with sodium borohydride is effected in methanol solution at about 0°C, for a period of time of the order of 30 minutes to several hours, preferably for about one to two hours, using at least 1.1 molar equivalents of the reagent per mol of 9-keto starting compound, to give a mixture of the corresponding 9α and 9β-hydroxy derivatives, which is separated into the individual isomers by chromatography on Florisil or thin layer chromatography.

The reduction with zinc borohydride is effected preferably in dimethoxyethane solution using an excess of the reagent (prepared from freshly fused zinc chloride and sodium borohydride in dimethoxyethane) under anhydrous conditions, at temperatures in the range of 5° to 25°C, for about from 15 minutes to 3 hours, obtaining also a mixture of the corresponding 9α- and 9β-hydroxy compounds which can be separated into the individual isomers by chromatographic techniques, as previously mentioned.

The zinc borohydride reduction method is preferred when using a 9-keto-11α-halomethyl-prostaglandin derivative (XIII, X = Cl, Br, F) as starting material.

Compounds of formula XIV ($R^{6'}$ = Me) are converted into the corresponding 15-keto derivatives of formula XV by selective oxidation of the 15-hydroxy group with an excess of 2,3-dichloro-5,6-dicyano-1,4-benzoquinone in benzene or dioxane as solvents, conducting the reaction at a temperature above room temperature, i.e., at about 50° to 60°C for a period of time of the order of 14 to 20 hours, preferably for about 18 hours. The course of the reaction can be followed by thin layer chromatography or by periodic determination of the ultraviolet spectrum. When the reaction is complete, the product is isolated from the reaction mixture by conventional techniques, such as separation of the insoluble material by filtration, evaporation of the filtrate and purification of the residue by chromatographic techniques.

Alternatively, the selective oxidation at C-15 can be effected with manganese dioxide in chloroform or tetrahydrofuran solution, at room temperature for 18 to 40 hours.

Treatment of the 15-keto compounds of formula XV with an excess of an alkylmagnesium halide, i.e., methyl or ethylmagnesium bromides or chlorides, yields the corresponding 15ξ-alkyl-15ξ-hydroxy compounds of formula XVI ($R^2$ = Me, Et; $R^{6'}$ = Me), as mixtures of the respective 15α-hydroxy-15β-alkyl- and 15β-hydroxy-15α-alkyl isomers. This reaction is preferably carried out in ether or tetrahydrofuran solution, using from 6 to 18 molar equivalents of the Grignard reagent per molar equivalent of starting compound, at a temperature of between −25°C to room temperature, for a period of time of 1 to 4 hours, under an inert atmosphere.

Typically, the reaction is conducted by adding the Grignard reagent, portionwise, to a previously cooled solution (−20°C) of a compound of formula XV in diethylether or tetrahydrofuran, under argon or nitrogen atmosphere. The temperature of the reaction mixture is then allowed to rise to about −5°C, an additional amount of the Grignard reagent is added, following the course of the reaction by thin layer chromatographic techniques, the reaction being generally complete within about 2 hours.

Alternatively, the reaction can be carried out using a molar excess of an alkyllithium as reagent, i.e., methyl- or ethyllithium, conducting the reaction at about −70° to 20°C, for a short period of time, of the order of 10 to 30 minutes; however, a more selective alkylation is obtained when using a Grignard reagent.

The mixture of 15α-hydroxy-15β-alkyl- and 15β-hydroxy-15α-alkyl compounds of formula XVI ($R^{6'}$ = Me) is separated into the individual isomers by thin layer chromatography.

Upon oxidation of compounds of formula XVI ($R^{6'}$ = Me) with chromium trioxide under alkaline conditions there are produced the corresponding 9-keto derivatives of formula XVII ($R^{6'}$ = Me). Suitable oxidizing agents are, for example, chromium trioxide-pyridine complex, chromium trioxide-dipyridine complex (Collins' reagent) and dicyclohexylcarbodiimide or diisopropylcarbodiimide in dimethyl sulfoxide (Moffat's reagent), using particularly chromium trioxide-dipyridine complex, conducting the reaction at low temperature, in the range of 10° to 0°C, for a short period of time, of the order of 5 to 20 minutes.

The methyl ester compounds of formula XIV, XVI and XVII ($R^{6'}$ = Me) are converted into the respective free prost-13-trans-enoic and prosta-5-cis,13-trans-dienoic acids of the invention (XIV, XVI and XVII, $R^{6'}$ = H) preferably by enzymatic hydrolysis methods, using for example, a recently extracted residue of the gorgonian Plexaura homomalla (Esper), in a saline solution, at a pH 7.5 to 7.7 as described by A. Prince et al, in *Prostaglandins*, Vol. 3, No. 4 p. 531 (1973), which method has also been mentioned hereinbefore for the hydrolysis of the methyl ester group in the 9-keto compounds of the invention non-alkylated at C-15, or other enzyme systems which are known as useful for the hydrolysis of compounds unstable to alkaline or acid conditions, such as a crude pancreatic lipase commercially available (Sigma Steapsin), a crude hog pancreatic lipase, by the method described by A. F. Kluge et al., in *J. Am. Chem. Soc.* 94, 782 (1972) or baker's yeast [C. J. Sih et al., *J. C. S. Chem. Comm.* 240 (1972)].

The methyl ester group in compounds of formulas XIV, XVI and XVII ($R^{6'}$ = Me, X = azido, lower alkoxy, thiomethyl, formamido, alkylamido, methylsulfinyl or methylsulfonyl) can also be hydrolyzed chemically, by treatment with potassium carbonate in aqueous methanol, for about 12 to 24 hours, preferably for about 16 hours, at room temperature and under nitrogen or argon atmosphere, followed by careful acidification with a weak acid, such as acetic acid. In the case of compounds XVI and XVII, this acidification is effected at low temperature, i.e., at about 0° to −10°C, to avoid dehydration of the tertiary hydroxyl group at C-15.

The 11α-aminomethyl and substituted aminomethyl prostadienoic and prostenoic acid methyl ester compounds of formulas XII ($R^{6'}$ = Me; $R^7$ = H), XIV, XVI and XVII

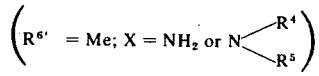

can be converted into the free acids of saponification with sodium or potassium carbonate, as previously described with regard to other compounds of the invention, followed by evaporation of the solvent, disolution of the residue in water and filtration of the aqueous solution through a column of an strongly acidic cation exchange resin (in $H^+$ form) such as Amberlite or Dowex 50, acid form (+), eluting the column first with water and thereafter with dilute acetic acid, e.g., 10% aqueous acetic acid. The acidic eluates afford, after lyophilization, the desired free acids (XII, $R^{6'}$ and $R^7$ = H; XIV, XVI and XVII,

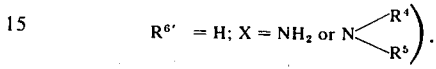

The alkyl esters of the carboxylic acid function in the novel compounds of the present invention other than the methyl ester can be prepared by treatment of the free acid with an excess of a diazoalkane such as diazoethane or diazopropane in ether or methylene chloride solution, in a conventional manner, or by reaction with the desired lower alkyl iodide in the presence of lithium carbonate, at room temperature.

The salt derivatives of the prostenoic and prostadienoic acids of the present invention can be prepared by treating the corresponding free acids with about one molar equivalent of a pharmaceutically acceptable base per molar equivalent of free acid. Suitable pharmaceutically acceptable bases include, for example, sodium hydroxide, trimethylamine, triethylamine, tripropylamine, β-(dimethylamino) ethanol, β-(diethylamino)ethanol, arginine, lysine, caffeine, procaine and the like. Typically, the reaction is conducted in an aqueous solution, alone or in combination with an inert water miscible organic solvent, at a temperature of about from 0° to 30°C, preferably at room temperature. Typical inert, water miscible organic solvents includes methanol, ethanol, isopropanol, butanol, dioxane and the like. When divalent metal salts are prepared such as the calcium salts or magnesium salts, the free acid starting material is treated with at least one half molar equivalent of the pharmaceutically acceptable base.

In conducting the above-described processes, it is generally preferred to separate or isolate the respective products of each reaction step prior to their use as starting materials in subsequent steps. Illustrative non-limiting separation and isolation procedures can be had by reference to the appropriate Examples set forth hereinbelow. Also, when the starting compound is an 8R-antimer, the products obtained are 8R-antimers, while when using a racemic compound as starting material the products obtained are racemates.

The compounds of formula I used as starting materials in the above described processes can be obtained in accordance with copending patent application Ser. No. 447,323, filed Mar. 1, 1974, of Guzman and Marx, which involves sensitized irradiation of natural $PGA_2$ methyl ester [isolated from the gorgonian Plexaura homomalla (Esper)] or its racemate in methanol solution, in the presence of benzophenone or another sensitizing agent, at a wavelenght of about 360 mμ, or by the method described in our copending patent application Ser. No. 444,689 filed Feb. 21, 1974.

The compounds, esters and salts of the invention exhibit prostaglandin-like biological activities and thus are useful in the treatment of mammals where the use of prostaglandins are indicated. The compounds, esters and salts of the invention are bronchodilators and thus are useful in treating mammals for bronchial spasm or wherever strong bronchodilators are indicated. These compounds are also useful in controlling or palliating hypertension in mammals and further exhibit central nervous system depressant activity in mammals, and are useful as sedatives. In addition, the compounds are useful for inducing labor, in pregnancy and for inducing menses to correct or reduce menstrual abnormalities.

The compounds and/or salts of the invention, can be administered in a wide variety of dosage forms, either alone or in combination with other pharmaceutically compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid or aerosol, in which the compound and/or salt is dissolved, dispersed or suspended, and can optionally contain small amounts of preservatives and/or pH-buffering agents. Suitable preservatives which can be used include, for example benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the compounds and/or salts can, for example, be administered as an aerosol comprising the compounds or salts in an inert propellant together with a cosolvent (e.g. ethanol) together with optional preservatives and buffering agents. Additional general information concerning the inhalation administration of aerosols can be had by reference to U.S. Pat. Nos. 2,868,691 and 3,095,355.

The compounds of this invention are typically administered in dosages of about from 0.1 to 10 mg. per Kg. of body weight. The precise effective dosage will, of course, vary depending upon the mode of administration, condition being treated and host.

The following Examples illustrate the invention, but are not intended to limit its scope. The abbreviation t.l.c. refers to thin-layer chromatography and all mixture ratios used with regard to liquids refer to volume ratios. Also, where necessary, examples are repeated to provide sufficient starting material for subsequent examples.

PREPARATION 1

To a solution of 250 mg. of 8R-9-keto-15α-hydroxyprosta-5-cis,10,13-trans-trienoic acid methyl ester [natural PGA$_2$ methyl ester, isolated from the gorgonian *Plexaura homomalla* (Esper) and purified by successive chromatographies, first on a Florisil column using increasing percentages of ether in methanol and thereafter by thin-layer chromatography on silica gel, using methylene chloride-ethyl acetate (95:5) as gradient] in 40 ml. of anhydrous methanol, placed into a Pyrex vessel of an irradiation apparatus are added 30 mg. of benzophenone. Nitrogen is then bubbled through the resulting mixture for 15 minutes, and thereafter it is irradiated at 360 mμ for 6 hours using a G. E. germicidal lamp F 4T5-BLB. At the end of this time the reaction is essentially complete as demonstrated by the substantial extinction of the ultraviolet absorption at 217 mμ. The reaction mixture is then evaporated to drynes under reduced pressure and the residue purified by t.l.c. using ethyl acetate-methanol (99.5:0.5) as eluant, thus yielding the pure 8R-9-keto-11α-hydroxymethyl-15α-hydroxyprosta-5-cis,13-trans-dienoic acid methyl ester.

In a similar manner, starting from 9-keto-15α-hydroxyprosta-5-cis,10,13-trans-trienoic acid methyl ester [obtained by dehydration of racemic PGE$_2$ with 90% aqueous acetic acid, in accordance with the method of J. E. Pike et al., *J. Org. Chem.* 34, 3552 (1969) followed by conventional esterification of the carboxylic acid function with ethereal diazomethane] there is obtained 9-keto-11α-hydroxymethyl-15α-hydroxyprosta-5-cis,13-trans-dienoic acid methyl ester in similar yield.

EXAMPLE 1

A. To a solution of 170 mg. of 8R-9-keto-11α-hydroxymethyl-15α-hydroxyprosta-5-cis,13-trans-dienoic acid methyl ester in 5 ml. of pyridine are added 5 ml. of acetic anhydride and the reaction mixture is kept at room temperature for 2 hours. It is then evaporated to dryness under vacuo, the oily residue is dissolved in ethyl acetate and the resulting solution washed with 1% hydrochloric acid solution, sodium bicarbonate solution and saturated sodium chloride solution, dried over sodium sulfate and evaporated to dryness under vacuo, thus obtaining 8R-9-keto-11α-acetoxymethyl-15α-acetoxyprosta-5-cis,13-trans-dienoic acid methyl ester.

B. To a solution of 46.4 mg. of 8R-9-keto-11α-acetoxymethyl-15α-acetoxyprosta-5-cis,13-trans-dienoic acid methyl ester in 3 ml. of anhydrous methanol is added, under nitrogen atmosphere, 6.9 mg. (1 equivalent) of potassium carbonate. The resulting mixture is stirred at room temperature for 2 hours. It is then diluted with 40 ml. of ethyl acetate and acidified with 1% hydrochloric acid solution, the organic phase is separated and washed with water to neutral, dried over sodium sulfate and evaporated to dryness under reduced pressure. The residue is purified by t.l.c., using hexane-ethyl acetate (1:1) as gradient to produce the pure 8R-9-keto-11α-hydroxymethyl-15α-acetoxyprosta-5-cis,13-trans-dienoic acid methyl ester (8R-antimer of II, Z = double bond).

In a similar manner 9-keto-11α-hydroxymethyl-15α-hydroxyprosta-5-cis,13-trans dienoic acid methyl ester is converted into 9-keto-11α-hydroxymethyl-15α-acetoxyprosta-5-cis,13-trans-dienoic acid methyl ester.

EXAMPLE 2

A. To a prehydrogenated suspension of 14 mg. of 5% palladium charcoal catalyst in 5 ml. of methanol is added a solution of 140 mg. of 8R-9-keto-11α-hydroxymethyl-15α-acetoxyprosta-5-cis,13-trans-dienoic acid methyl ester in 10 ml. of methanol and the resulting mixture is stirred under hydrogen atmosphere until 1 mol of hydrogen is absorbed. The catalyst is then separated by filtration through Celite, diatomaceous earth, washing the solid material with methanol. The combined organic filtrates are evaporated to dryness under reduced pressure and the residue purified by t.l.c., to afford 8R-9-keto-11α-hydroxymethyl-15α-acetoxyprost-13-trans-enoic acid methyl ester in pure form (8R-antimer of II, Z = saturated linkage).

B. Fifteen milligrams of 8R-9-keto-11α-hydroxymethyl-15α-acetoxyprosta-5-cis,13-trans-dienoic acid methyl ester are dissolved in a mixture of 2 ml. of benzene and 3 ml. of acetone containing 5 mg. of freshly prepared tris-(triphenylphosphine) chlororhodium, at room temperature. The resulting mixture is stirred in a hydrogen atmosphere and aliquots are removed at periodic intervals. The aliquots are analyzed by gas liquid chromatography to determine whether hydrogenation has been completed. When the hydrogenation is determined to be essentially complete (ca. six hours) the reaction mixture is applied to 20% wt. silver nitrate impregnated silica gel (G) preparative plates developing with chloroform:methanol:acetic acid:water in a 95:75:1:0.6 parts by volume ratio. The zone corresponding to the desired monounsaturated compound is eluted with a 90:10, by vol., of a mixture of chloroform and methanol yielding the pure 8R-9-keto-11α-hydroxymethyl-15α-acetoxyprost-13-trans-enoic acid methyl ester, identical to the product obtained in part A.

EXAMPLE 3

To a solution of 315 mg. of triphenylphosphine in 10 ml. of anhydrous dimethoxyethane is passed a slow stream of anhydrous chlorine gas until the solution becomes pale yellow. A few crystals of triphenylphosphine are added to discharge the color and the solution is cooled to 0°C. To the cold solution are added 314 mg. of 8R-9-keto-11α-hydroxymethyl-15α-acetoxyprosta-5-cis,13-trans-dienoic acid methyl ester dissolved in 3 ml. of anhydrous dimethoxyethane and the reaction mixture is stirred at 0°C for 30 minutes. The solvent is then eliminated under reduced pressure and the oily residue purified by thin layer chromatography, using hexane-ethyl acetate (75:25) as gradient to produce 8R-9-keto-11α-chloromethyl-15α-acetoxyprosta-5-cis,13-trans-dienoic acid methyl ester (8R-antimer of III, $R^{6'}$ = methyl; $R^7$ = Ac; $X'$ = chloro; Z = double bond).

In a similar manner, 9-keto-11α-hydroxymethyl-15α-acetoxyprosta-5-cis,13-trans-dienoic acid methyl ester is converted into 9-keto-11α-chloromethyl-15α-acetoxyprosta-5-cis,13-trans-dienoic acid methyl ester.

EXAMPLE 4

A solution of 196.5 mg. of triphenylphosphine in 10 ml. of dimethoxyethane is treated with bromine, in a dropwise fashion, until the solution is slightly yellow. A few crystals of triphenylphosphine are added to decolorize the solution which is then cooled to 0°C. To the cold solution is added a solution of 227 mg. of 8R-9-keto-11α-hydroxymethyl-15α-acetoxyprosta-5-cis,13-trans-dienoic acid methyl ester in 3 ml. of dimethoxyethane, and the reaction mixture is maintained at 0°C for 30 minutes. It is then evaporated to dryness under vacuo and the residue purified by t.l.c. using hexaneethyl acetate (70:30) as eluant, to obtain the pure 8R-9-keto-11α-bromomethyl-15α-acetoxyprosta-5-cis,13-trans-dienoic acid methyl ester (8R-antimer of III, $R^{6'}$ = Me; $R^7$ = Ac; $X'$ = bromo; Z = double bond).

By the same method, 9-keto-11α-hydroxymethyl-15α-acetoxyprosta-5-cis,13-trans-dienoic acid methyl ester, 8R-9-keto-11α-hydroxymethyl-15α-acetoxyprost-13-trans-enoic acid methyl ester and 9-keto-11α-hydroxymethyl-15α-acetoxyprost-13-transenoic acid methyl ester, are converted respectively into:

9-keto-11α-bromomethyl-15α-acetoxyprosta-5-cis,13-trans-dienoic acid methyl ester, 8R-9-keto-11α-bromomethyl-15α-acetoxyprost-13-trans-enoic acid methyl ester and 9-keto-11α-bromomethyl-15α-acetoxyprost-13-trans-enoic acid methyl ester.

EXAMPLE 5

To a solution of 100 mg. of 8R-9-keto-11α-hydroxymethyl-15α-acetoxyprosta-5-cis,13-trans-dienoic acid methyl ester in 5 ml. of dry carbon tetrachloride is added 75.1 mg. of triphenylphosphine and the reaction mixture is refluxed under anhydrous conditions for 20 minutes. It is then evaporated to dryness under reduced pressure and the residue purified by t.l.c. using hexaneethyl acetate (75:25) as gradient, to produce 8R-9-keto-11α-chloromethyl-15α-acetoxyprosta-5-cis,13-trans-dienoic acid methyl ester, identical to the product obtained in Example 3.

By the same method but using carbon tetrabromide in place of carbon tetrachloride there is obtained 8R-9-keto-11α-bromomethyl-15α-acetoxyprosta-5-cis,13-trans-dienoic acid methyl ester, identical to the product obtained in Example 4.

EXAMPLE 6

To a solution of 422 mg. (1 mmol) of 8R-9-keto-11α-hydroxymethyl-15α-acetoxyprosta-5-cis,13-trans-dienoic acid methyl ester in 2 ml. of dimethylformamide is added 308 mg. of anhydrous carbon tetrachloride. The solution is cooled to −40° to −45°C and then treated dropwise, under nitrogen atmosphere and with stirring, with 261 mg. of tris(dimethylamino)phosphine in 1 ml. of dimethylformamide. The course of the reaction is followed by thin layer chromatography. After about one hour, the reaction is essentially complete. To the reaction mixture are then added 170 mg. of lithium chloride, and the reaction mixture is stirred for 24 hours at 110°C. The solvent is eliminated under vacuo and the residue is taken up in ethyl acetate. The organic solution is washed with sodium chloride solution, dried and evaporated to dryness under vacuo. Purification of the residue by t.l.c. as described in Example 3, affords the pure 8R-9-keto-11α-chloromethyl-15α-acetoxyprosta-5-cis,13-trans-dienoic acid methyl ester, identical to the product obtained in said Example.

In a similar manner but using equivalent amounts of carbon tetrabromide and lithium bromide instead of carbon tetrachloride and lithium chloride, respectively, there is obtained 8R-9-keto-11α-bromomethyl-15α-acetoxyprosta-5-cis,13-trans-dienoic acid methyl ester.

EXAMPLE 7

A. To a magnetically stirred solution of 100 mg. of 8R-9-keto-11α-hydroxymethyl-15α-acetoxyprosta-5-cis,13-trans-dienoic acid methyl ester in 5 ml. of carbon tetrachloride is added 46.4 mg. of tri-n-octylphosphine and the reaction mixture is maintained at room temperature for 15 minutes. It is then evaporated to dryness under vacuo and the residue purified by t.l.c.

using hexane-ethyl acetate (75:25) as gradient, to yield 8R-9-keto-11α-chloromethyl-15α-acetoxyprosta-5-cis,13-trans-dienoic acid methyl ester, identical to the product obtained in Example 3.

By the same method, 8R-9-keto-11α-hydroxymethyl-prost-13-trans-enoic acid methyl ester and its racemate are converted into the corresponding 11α-chloromethyl derivatives.

B. To a magnetically stirred solution of 422 mg. of 8R-9-keto-11α-hydroxymethyl-15α-acetoxyprosta-5-cis,13-trans-dienoic acid methyl ester in 5 ml. of anhydrous ether and 664 mg. of carbon tetrabromide is added 392 mg. of tri-n-octylphosphine. An immediate exothermic reaction takes place and the initially colorless mixture turns yellow. Five minutes after complete addition of the phosphine the reaction appears to be essentially complete, as demonstrated by t.l.c. analysis. The solvent is eliminated under reduced pressure and the residue purified by thin layer chromatography, to obtain the pure 8R-9-keto-11α-bromomethyl-15α-acetoxyprosta-5-cis,13-trans-dienoic acid methyl ester, identical to the product obtained in Example 4.

EXAMPLE 8

A. A solution of 195 mg. of 8R-9-keto-11α-bromomethyl-15α-acetoxyprosta-5-cis,13-trans-dienoic acid methyl ester in 10 ml. of 90% aqueous acetone is treated with 500 mg. of sodium azide and the reaction mixture is refluxed for 17 hours. It is then cooled, poured into water and extracted with methylene chloride (3 × 30 ml.). The combined organic extracts are washed with saturated sodium chloride solution, dried over sodium sulfate and evaporated to dryness under reduced pressure. The residue is purified by t.l.c. using methylene chloride-methanol (99:1) as gradient to obtain the pure 8R-9-keto-11α-azidomethyl-15α-acetoxyprosta-5-cis,13-trans-dienoic acid methyl ester (8R-antimer of VI, $R^{6'}$ = Me; $R^7$ = Ac; Z = double bond).

B. A solution of 100 mg. of 8R-9-keto-11α-bromomethyl-15α-acetoxyprosta-5-cis,13-trans-dienoic acid methyl ester in 5 ml. of dimethylsulfoxide is mixed with a solution of 134 mg. of sodium azide in 0.7 ml. of water, and the resultant mixture is heated on a steam bath for 16 hours. The solution is poured into ice-water and extracted several times with ethyl acetate. The combined organic extracts are washed, dried and evaporated and the residue purified by t.l.c. as described in part A, to yield 8R-9-keto-11α-azidomethyl-15α-acetoxyprosta-5-cis,13-trans-dienoic acid methyl ester, identical to the product obtained in part A.

In another experiment the reaction was conducted at room temperature for 48 hours, obtaining the same results.

By following the methods of parts A or B of this Example,
9-keto-11α-bromomethyl-15α-acetoxyprosta-5-cis,13-trans-dienoic acid methyl ester,
8R-9-keto-11α-bromomethyl-15α-acetoxyprost-13-trans-enoic acid methyl ester and
9-keto-11α-bromomethyl-15α-acetoxyprost-13-trans-enoic acid methyl ester
are converted respectively into:
9-keto-11α-azidomethyl-15α-acetoxyprosta-5-cis,13-trans-dienoic acid methyl ester,
8R-9-keto-11α-azidomethyl-15α-acetoxyprost-13-trans-enoic acid methyl ester and
9-keto-11α-azidomethyl-15α-acetoxyprost-13-trans-enoic acid methyl ester.

EXAMPLE 9

To a solution of 447 mg. of 8R-9-keto-11α-azidomethyl-15α-acetoxyprosta-5-cis,13-trans-dienoic acid methyl ester in 10 ml. of anhydrous benzene is added 262 mg. of triphenylphosphine. A chip of porous porcelain is added to initiate the reaction, maintaining the reaction mixture at room temperature for 2 hours and then under refluxing conditions for an additional hour, at the end of which time the reaction is essentially complete, as demonstrated by thin layer chromatographic analysis. The reaction mixture is then evaporated to dryness under reduced pressure, and the oily residue dissolved in 10 ml. of 2% methanolic potassium hydroxide solution. The resultant reaction mixtue is refluxed for 3 hours under argon atmosphere, evaporated to dryness under reduced pressure and the residue dissolved in 20 ml. of water. The aqueous solution is passed through a column of 10 g. of ion exchange resin Dowex 50 acidic type ($H^+$), eluting the column first with water and thereafter with 10% acetic acid solution. The combined acidic eluates are concentrated to a small volume under reduced pressure, at low temperature, liophylized and purified by t.l.c. to yield the pure 8R-9-keto-11α-aminomethyl-15α-hydroxyprosta-5-cis,13-trans-dienoic acid (8R-antimer of VII, $R^{6'}$ and $R^7$ = H; Z = double bond).

In a similar manner,
9-keto-11α-azidomethyl-15α-acetoxyprosta-5-cis,13-trans-dienoic acid methyl ester,
8R-9-keto-11α-azidomethyl-15α-acetoxyprost-13-trans-enoic acid methyl ester and
9-keto-11α-azidomethyl-15α-acetoxyprost-13-trans-enoic acid methyl ester,
are converted respectively into:
9-keto-11α-aminomethyl-15α-hydroxyprosta-5-cis,13-trans-dienoic acid,
8R-9-keto-11α-aminomethyl-15α-hydroxyprost-13-trans-enoic acid and
9-keto-11α-aminomethyl-15α-hydroxyprost-13-trans-enoic acid.

EXAMPLE 10

A mixture of 200 mg. of 8R-9-keto-11α-aminomethyl-15α-hydroxyprosta-5-cis,13-trans-dienoic acid, 0.4 ml. of acetic anhydride and 0.8 ml. of pyridine is kept at room temperature for 1 hour. It is then evaporated to dryness under vacuo and the residue dissolved in ethyl acetate. The resulting solution is washed with 50% saturated sodium chloride solution, dried over sodium sulfate and evaporated to dryness under reduced pressure, to yield 8R-9-keto-11α-aminomethyl-15α-acetoxyprosta-5-cis,13-trans-dienoic acid.

The foregoing crude compound is dissolved in 5 ml. of methylene chloride, 1 ml. of ethereal diazomethane is added and the reaction mixture is kept at room temperature for 20 minutes. The solvents and excess reagent are eliminated by vacuum distillation, thus affording 8R-9-keto-11α-aminomethyl-15α-acetoxyprosta-5-cis,13-trans-dienoic acid methyl ester (8R-antimer of VII, $R^{6'}$ = Me; $R^7$ = Ac; Z = double bond).

In a similar manner, the remaining compounds obtained in Example 9 are converted respectively into;
9-keto-11α-aminomethyl-15α-acetoxyprosta-5-cis,13-trans-dienoic acid methyl ester, 8R-9-keto-11α-aminomethyl-15α-acetoxy-prost-13-trans-enoic acid methyl ester and
9-keto-11α-aminomethyl-15α-acetoxyprost-13-trans-enoic acid methyl ester.

EXAMPLE 11

A mixture of 100 mg. of 8R-9-keto-11α-aminomethyl-15α-acetoxyprosta-5-cis,13-trans-dienoic acid methyl ester, 3 ml. of pyridine and 3 ml. of acetic anhydride is kept at room temperature for 16 hours. The reaction mixture is then evaporated to dryness under reduced pressure and the residue dissolved in ethyl acetate. The organic solution is washed with 1% hydrochloric acid solution, sodium bicarbonate solution and sodium chloride solution, dried over sodium sulfate and evaporated to dryness under vacuo. The residue is purified by t.l.c. to afford the pure 8R-9-keto-11α-acetamidomethyl-15α-acetoxyprosta-5-cis,13-trans-dienoic acid methyl ester (8R-9-keto-11α-methylcarbonylaminomethyl-15α-acetoxyprosta-5-cis,13-trans-dienoic acid methyl ester) (8R-antimer of VIII, $R^{3'}$ and $R^{6'}$ = Me; $R^7$ = Ac; Z = double bond).

In another experiment acetyl chloride was substituted for acetic anhydride, obtaining the same results.

In a similar manner but using propionic anhydride, butanoic anhydride or valeric anhydride or the corresponding acid chlorides in place of acetic anhydride there are respectively produced:

8R-9-keto-11α-propionamidomethyl-15α-acetoxyprosta-5-cis,13-trans-dienoic acid methyl ester,
8R-9-keto-11α-butyramidomethyl-15α-acetoxyprosta-5-cis,13-trans-dienoic acid methyl ester and
8R-9-keto-11α-valeramidomethyl-15α-acetoxyprosta-5-cis,13-trans-dienoic acid methyl ester, By the same method but using the remaining 11α-aminomethyl compounds obtained in Example 10 as starting materials there are produced the respective alkylamido derivatives, e.g., 9-keto-11α-propionamidomethyl-15α-acetoxyprosta-5-cis,13-trans-dienoic acid methyl ester,
8R-9-keto-11α-acetamidomethyl-15α-acetoxyprost-13-trans-enoic acid methyl ester and
9-keto-11α-butyramidomethyl-15α-acetoxyprost-13-trans-enoic acid methyl ester.

EXAMPLE 12

A cold solution of 100 mg. of 8R-9-keto-11α-aminomethyl-15α-acetoxyprosta-5-cis,13-trans-dienoic acid methyl ester in 10 ml. of isopropyl ether is added dropwise, under stirring to 63.8 mg. (1.1 molar equivalents) of crude phenyl formate [prepared as described by H. L. Yale in *J. Org. Chem.*36, 3238 (1971)] cooled to 0°C. The temperature of the reaction mixture rises spontaneously to 25°C and is kept at this temperature for 16 hours. The solvent and excess reagent are distilled under vacuo, and the oily residue taken up in ethyl acetate. The organic extract is washed with sodium chloride solution, dried over sodium sulfate and evaporated to dryness under vacuo. Purification of the residue by t.l.c. affords 8R-9-keto-11α-formamidomethyl-15α-acetoxyprosta-5-cis,13-trans-dienoic acid methyl ester in pure form (8R-antimer of VIII, $R^{3'}$ = H; $R^{6'}$ = Me; $R^7$ = Ac; Z = double bond).

In a similar manner,
9-keto-11α-aminomethyl-15α-acetoxyprosta-5-cis,13-trans-dienoic acid methyl ester,
8R-9-keto-11α-aminomethyl-15α-acetoxyprost-13-trans-enoic acid methyl ester and
9-keto-11α-aminomethyl-15α-acetoxyprost-13-trans-enoic acid methyl ester,
are converted respectively into
9-keto-11α-formamidomethyl-15α-acetoxyprosta-5-cis,13-trans-dienoic acid methyl ester,
8R-9-keto-11α-formamidomethyl-15α-acetoxyprost-13-trans-enoic acid methyl ester and
9-keto-11α-formamidomethyl-15α-acetoxyprost-13-trans-enoic acid methyl ester.

EXAMPLE 13

To a solution of 100 mg. of 8R-9-keto-11α-hydroxymethyl-15α-acetoxyprosta-5-cis,13-trans-dienoic acid methyl ester in 5 ml. of anhydrous tetrahydrofuran are added, under nitrogen atmosphere, 10 mg. of sodium hydride and 1 ml. of methyl iodide, and the reaction mixture is stirred for 24 hours at room temperature, under anhydrous conditions. It is then evaporated to dryness under reduced pressure, the residue is dissolved in ethyl acetate and the organic solution washed with saturated sodium chloride solution, dried over sodium sulfate and evaporated to dryness under vacuo. The residue is purified ty t.l.c. to afford the pure 8R-9-keto-11α-methoxymethyl-15α-acetoxyprosta-5-cis,13-trans-dienoic acid methyl ester (8R-antimer of V, $R^1$ and $R^{6'}$ = Me; $R^7$ = Ac; Z = double bond).

In a similar manner but using ethyl iodide and isopropyl iodide in lieu of methyl iodide there are obtained 8R-9-keto-11α-ethoxymethyl-15α-acetoxyprosta-5-cis,13-trans-dienoic acid methyl ester and 8R-9-keto-11α-isopropoxymethyl-15α-acetoxyprosta-5-cis,13-trans-dienoic acid methyl ester, respectively.

By the same method from the corresponding 11α-hydroxymethyl compounds and using methyl iodide as alkylating agent there are obtained:

9-keto-11α-methoxymethyl-15α-acetoxyprosta-5-cis,13-trans-dienoic acid methyl ester,
8R-9-keto-11α-methoxymethyl-15α-acetoxyprost-13-trans-enoic acid methyl ester and
9-keto-11α-methoxymethyl-15α-acetoxyprost-13-trans-enoic acid methyl ester.

EXAMPLE 14

To 5 ml. of anhydrous methanol, cooled to 0°C, is added 0.2 ml. of methanethiol and 10 mg. of sodium methoxide and the resulting mixture is stirred for 5 minutes. To the sodium thiomethylate thus prepared is added dropwise, under nitrogen atmosphere and under stirring, a solution of 100 mg. of 8R-9-keto-11α-bromomethyl-15α-acetoxyprosta-5-cis,13-trans-dienoic acid methyl ester in 5 ml. of anhydrous methanol. The reaction mixture is kept at room temperature for 6 hours. It is then evaporated to dryness under reduced pressure and the residue dissolved in ethyl acetate. The organic solution is washed twice with sodium chloride solution, dried over sodium sulfate and evaporated to dryness under vacuo. Purification of the residue by t.l.c. affords the pure 8R-9-keto-11α-methylthiomethyl-15α-acetoxyprosta-5-cis,13-trans-dienoic acid methyl ester (8R-antimer of IX, $R^{6'}$ = Me; $R^7$ = Ac; Z = double bond).

In a similar manner, using the corresponding 11α-bromomethyl compounds as starting materials there are produced:
9-keto-11α-methylthiomethyl-15α-acetoxy-
prosta-5-cis,13-trans-dienoic acid methyl ester,
8R-9-keto-11α-methylthiomethyl-15α-acetoxy-
prost-13-trans-enoic acid methyl ester and
9-keto-11α-methylthiomethyl-15α-acetoxy-
prost-13-trans-enoic acid methyl ester.

EXAMPLE 15

To 1.1 ml. of a 0.5M solution of sodium metaperiodate cooled to 0°C is added dropwise, under stirring, a solution of 226 mg. of 8R-9-keto-11α-methylthiomethyl-15α-acetoxyprosta-5-cis,13-trans-dienoic acid methyl ester in 5 ml. of methanol, stirring the reaction mixture for 18 hours further in an ice bath. The insoluble material is separated by filtration, the filtrate is concentrated to a small volume under reduced pressure and extracted with methylene chloride. The organic extract is washed with sodium chloride solution, dried over sodium sulfate and evaporated to dryness under reduced pressure. The oily residue is purified by t.l.c., to afford the pure 8R-9-keto-11α-methylsulfinylmethyl-15α-acetoxyprosta-5-cis,13-trans-dienoic acid methyl ester (8R-antimer of X, $R^{6'}$ = Me; $R^7$ = acetyl; Z = double bond).

By the same method, starting from the remaining 11α-methylthiomethyl compounds obtained in Example 14 there are respectively prepared:
9-keto-11α-methylsulfinylmethyl-15α-acetoxy-
prosta-5-cis,13-trans-dienoic acid methyl ester,
8R-9-keto-11α-methylsulfinylmethyl-15α-
acetoxyprost-13-trans-enoic acid methyl ester and
9-keto-11α-methylsulfinylmethyl-15α-acetoxy-
prost-13-trans-enoic acid methyl ester.

EXAMPLE 16

To a stirred solution of 200 mg. of 8R-9-keto-11α-methylsulfinylmethyl-15α-acetoxyprosta-5-cis,13-trans-dienoic acid methyl ester in 20 ml. of anhydrous methanol, cooled to 0°C is added portionwise, 62.7 mg. of N-chlorosuccinimide, maintaining the temperature of the reaction mixture below 10°C. When all the reagent is added, the reaction mixture is kept at room temperature for an addition hour. The solvent is eliminated under reduced pressure and the residue is extracted with ether to effect separation of the product from the succinimide formed during the reaction. The organic extract is washed with sodium chloride solution, dried and evaporated to dryness under vacuo. The residue is purified by t.l.c., to afford the pure 8R-9-keto-11α-methylsulfonylmethyl-15α-acetoxyprosta-5-cis,13-trans-dienoic acid methyl ester (8R-antimer of XI, $R^{6'}$ = Me; $R^7$ = Ac; Z = double bond). In a similar manner, but using the remaining 11α-methylsulfinylmethyl compounds obtained in Example 15, there are respectively prepared:
9-keto-11α-methylsulfonylmethyl-15α-acetoxyprosta-5-cis,13-trans-dienoic acid methyl ester,
8R-9-keto-11α-methylsulfonylmethyl-15α-
acetoxyprost-13-trans-enoic acid methyl ester, and
9-keto-11α-methylsulfonylmethyl-15α-acetoxyprost-13-trans-enoic acid methyl ester.

EXAMPLE 17

A. To a stirred solution of 422 mg. of 8R-9-keto-11α-hydroxymethyl-15α-acetoxyprosta-5-cis,13-trans-dienoic acid methyl ester in 5 ml. of carbon tetrachloride and 5 ml. of anhydrous dimethylformamide cooled to −60°C is added under nitrogen atmosphere, 163 mg. of tris(dimethylamino)phosphine, maintaining the temperature of the reaction mixture at −8° to 65°C. When the addition is complete there is added a solution of 117 mg. of ammonium perchlorate in 2 ml. of anhydrous dimethylformamide. The ammonium chloride is separated by filtration and washed with 5 ml. of dimethylformamide.

B. To the combined organic filtrates, cooled to 0°C is added 90 mg. of dimethylamine in 2 ml. of dimethylformamide, under stirring, maintaining the temperature of the reaction mixture at a temperature not higher than 20°C. The reaction mixture is then heated at 80°C for 10 hours, cooled and diluted with water. It is then extracted with ether, and the organic extract washed with sodium chloride solution, dried over sodium sulfate and evaporated to dryness under vacuo. The residue is purified by t.l.c., to afford the pure 8R-9-keto-11α-N,N-dimethylaminomethyl-15α-acetoxyprosta-5-cis,13-trans-dienoic acid methyl ester (8R-antimer of XII, $R^4$, $R^5$ and $R^{6'}$ = Me; $R^7$ = Ac; Z = double bond).

By the same method but using 2 molar equivalents of diethylamine, methylethylamine, dipropylamine and methylbutylamine in lieu of dimethylamine there are respectively obtained:
8R-9-keto-11α-N,N-diethylaminomethyl-15α-
acetoxyprosta-5-cis,13-trans-dienoic acid methyl ester,
8R-9-keto-11α-N-methyl-N-ethylaminomethyl-
15α-acetoxyprosta-5-cis,13-trans-dienoic acid methyl ester,
8R-9-keto-11α-N,N-dipropylaminomethyl-
15α-acetoxyprosta-5-cis,13-trans-dienoic acid methyl ester and
8R-9-keto-11α-N-methyl-N-butylaminomethyl-
15α-acetoxyprosta-5-cis,13-trans-dienoic acid methyl ester.

In a similar manner but using 9-keto-11α-hydroxymethyl-15α-acetoxyprosta-5-cis,13-trans-dienoic acid methyl ester and 8R-9-keto-11α-hydroxymethyl-15α-acetoxyprost-13-trans-enoic acid methyl ester as starting materials there are obtained the corresponding 11α-N,N-disubstituted aminomethyl derivatives, namely:
9-keto-11α-N,N-dimethylaminomethyl-15α-
acetoxyprosta-5-cis,13-trans-dienoic acid methyl ester,
9-keto-11α-N,N-diethylaminomethyl-15α-
acetoxyprosta-5-cis,13-trans-dienoic acid methyl ester,
9-keto-11α-N-methyl-N-ethylaminomethyl-
15α-acetoxyprosta-5-cis,13-trans-dienoic acid methyl ester,
9-keto-11α-N,N-dipropylaminomethyl-15α-
acetoxyprosta-5-cis,13-trans-dienoic acid methyl ester,
9-keto-11α-N-methyl-N-butylaminomethyl-
15α-acetoxyprosta-5-cis,13-trans-dienoic acid methyl ester,
8R-9-keto-11α-N,N-dimethylaminomethyl-
15α-acetoxyprost-13-trans-enoic- acid methyl ester,
8R-9-keto-11α-N,N-diethylaminomethyl-15α-
acetoxyprost-13-trans-enoic acid methyl ester,
8R-9-keto-11α-N-methyl-N-ethylaminomethyl-
15α-acetoxyprost-13-trans-enoic acid methyl ester, 8R-9-keto-11a-N,N-dipropylaminomethyl-15a-acetoxyprost-13-trans-enoic acid methyl ester, and 8R-9-keto-11a-N-methyl-N-butylaminomethyl-15a-acetoxyprost-13-trans-enoic acid methyl ester.

EXAMPLE 18

Example 17 is repeated but using 2 molar equivalents of methylamine in lieu of dimethylamine thus obtaining 8R-9-keto-11a-N-methylaminomethyl-15a-acetoxyprosta-5-cis,13-trans-dienoic acid methyl ester (8R-antimer of XII, $R^5$ = H, $R^4$ and $R^{6'}$ = Me; $R^7$ = Ac; Z = double bond).

In a similar manner but using ethylamine, isopropylamine and t-butylamine in place of dimethylamine there are respectively obtained:

8R-9-keto-11a-N-ethylaminomethyl-15a-acetoxyprosta-5-cis,13-trans-dienoic acid methyl ester, 8R-9-keto-11a-N-isopropylaminomethyl-15a-acetoxyprosta-5-cis,13-trans-dienoic acid methyl ester, and 8R-9-keto-11a-N-t-butylaminomethyl-15a-acetoxyprosta-5-cis,13-trans-dienoic acid methyl ester.

By the same method but using 8R-9-keto-11a-hydroxymethyl-15a-acetoxyprost-13-trans-enoic acid methyl ester and 9-keto-11a-hydroxymethyl-15a-acetoxyprosta-5-cis,13-trans-dienoic acid methyl ester as starting materials there are obtained the corresponding 11a-N-methylaminomethyl-, N-ethylaminomethyl-, N-isopropylaminomethyl and N-t-butylaminomethyl derivatives.

EXAMPLE 19

To a solution of 200 mg. of 8R-9-keto-11a-azidomethyl-15a-acetoxyprosta-5-cis,13-trans-dienoic acid methyl ester in 10 ml. of anhydrous methanol is added under nitrogen atmosphere, 30 mg. of anhydrous potassium carbonate and the reaction mixture is stirred at room temperature for 90 minutes. It is then poured into water and extracted with ethyl acetate. The combined organic extracts are washed with saturated sodium chloride solution, dried over sodium sulfate and evaporated to dryness under vacuo. The oily residue is purified by t.l.c., to afford 8R-9-keto-11a-azidomethyl-15a-hydroxyprosta-5-cis,13-trans-dienoic acid methyl ester (8R-antimer of VI, $R^{6'}$ = Me; $R^7$ = H; Z = double bond) in pure form.

EXAMPLE 20

A mixture of 200 mg. of 8R-9-keto-11a-azidomethyl-15a-acetoxyprosta-5-cis,13-trans-dienoic acid methyl ester, 10 ml. of methanol and 2 molar equivalents of sodium hydroxide (in the form of a 2M solution) is kept at room temperature, under nitrogen atmosphere for 7 hours, one additional molar equivalent of sodium hydroxide is added and the reaction mixture is allowed to stand under the same conditions for 19 hours further. It is then concentrated to a small volume, diluted with water and extracted with ethyl acetate to eliminate the unsaponifiable products. The aqueous phase is acidified with oxalic acid and extracted with ethyl acetate. The organic extract is washed with sodium chloride solution, dried over sodium sulfate and evaporated to dryness under reduced pressure. The residue is purified by t.l.c. using a mixture of hexane-ethyl acetateacetic acid (50:50:2.5) as eluant, to obtain the pure 8R-9-keto-11a-azidomethyl-15a-hydroxyprosta-5-cis,13-trans-dienoic acid (8R-antimer of VI, $R^{6'}$ and $R^7$ = H; Z = double bond).

By the same method, starting from the corresponding methyl esters of 11a-(substituted) methyl-15a-acetoxyprostadienoic and prostenoic acids of Examples 8, 11, 12, 13, 14, 15 and 16 there are obtained:

9-keto-11a-azidomethyl-15a-hydroxyprosta-5-cis,13-trans-dienoic acid, 8R-9-keto-11a-azidomethyl-15a-hydroxyprost-13-trans-enoic acid, 8R-9-keto-11a-acetamidomethyl-15a-hydroxyprosta-5-cis, 13-trans-dienoic acid, 8R-9-keto-11a-propionamidomethyl-15a-hydroxyprosta-5-cis,13-trans-dienoic acid, 9-keto-11a-butyramidomethyl-15a-hydroxyprost-13-trans-enoic acid, 8R-9-keto-11a-formamidomethyl-15a-hydroxyprosta-5-cis, 13-trans-dienoic acid, 8R-9-keto-11a-formamidomethyl-15a-hydroxyprost-13-trans-enoic acid, 9-keto-11a-formamidomethyl-15a-hydroxyprosta-5-cis,13-trans-dienoic acid, 8R-9-keto-11a-methoxymethyl-15a-hydroxyprosta-5-cis,13-trans-dienoic acid, 8R-9-keto-11a-methoxymethyl-15a-hydroxyprost-13-trans-enoic acid, 9-keto-11a-ethoxymethyl-15a-hydroxyprosta-5-cis,13-trans-dienoic acid, 8R-9-keto-11a-methylthiomethyl-15a-hydroxyprosta-5-cis,13-trans-dienoic acid, 8R-9-keto-11a-methylthiomethyl-15a-hydroxyprost-13-trans-enoic acid, 9-keto-11a-methylthiomethyl-15a-hydroxyprosta-5-cis,13-trans-dienoic acid, 8R-9-keto-11a-methylsulfinylmethyl-15a-hydroxyprosta-5-cis,13-trans-dienoic acid, 8R-9-keto-11a-methylsulfinylmethyl-15a-hydroxyprost-13-trans-enoic acid, 9-keto-11a-methylsulfinylmethyl-15a-hydroxyprosta-5-cis,13-trans-dienoic acid, 8R-9-keto-11a-methylsulfonylmethyl-15a-hydroxyprosta-5-cis,13-trans-dienoic acid, 8R-9-keto-11a-methylsulfonylmethyl-15a-hydroxyprost-13-trans-enoic acid, and 9-keto-11a-methylsulfonylmethyl-15a-hydroxyprosta-5-cis,13-trans-dienoic acid.

EXAMPLE 21

A mixture of 150 mg. of 8R-9-keto-11a-chloromethyl-15a-acetoxyprosta-5-cis,13-trans-dienoic acid methyl ester, 3 g. of aged finely ground extracted residue of the gorgonian *plexaura homomalla* (Esper), [which results after extraction of the prostaglandin derivatives contained originally by this gorgonian, as described by A. Prince et al., in *Prostaglandins*, Vol. 3, No. 4, p. 531 (1973), dried at room temperature in the open for about 3 months] and 10 ml. of a 0.1M sodium chloride and 0.05M calcium chloride solution in water is stirred at room temperature for 24 hours. At the end of this time the reaction mixture is diluted with 15 ml. of acetone and the insoluble material separated by filtration through Celite, diatomaceous earth, washing the solids with several portions of acetone. The combined filtrates are concentrated under reduced pressure to a small volume, and the product extracted from the aqueous residue with methylene chloride. The combined organic extracts are dried over magnesium sulfate and evaporated to dryness under reduced pressure. The oily residue is purified by t.l.c., thus obtaining the pure 8R-9-keto-11a-chloromethyl-15a-hydroxyprosta-5-cis,13-trans-dienoic acid methyl ester (8R-antimer of III, $R^{6'}$ = Me; $R^7$ = H; X' = chloro; Z = double bond).

By the same method, from the corresponding 15a-acetoxy derivatives there are produced:
  8R-9-keto-11a-bromomethyl-15a-hydroxy-prosta-5-cis,13-trans-dienoic acid methyl ester,
  8R-9-keto-11a-chloromethyl-15a-hydroxy-prost-13-trans-enoic acid methyl ester,
  8R-9-keto-11a-bromoethyl-15a-hydroxyprost-13-trans-enoic acid methyl ester and the corresponding racemic compounds.

EXAMPLE 22

In accordance with the methods of Examples 19 or 21, the 15a-acetoxy function in the compounds obtained in Examples 10 to 18 is hydrolyzed, to yield the respective 15a-hydroxy derivatives. Representative compounds thus obtained are:
  8R-9-keto-11a-aminomethyl-15a-hydroxy-prosta-5-cis,13-trans-dienoic acid methyl ester,
  8R-9-keto-11a-aminomethyl-15a-hydroxy-prost-13-trans-enoic acid methyl ester,
  8R-9-keto-11a-acetamidomethyl-15a-hydroxy-prosta-5-cis,13-trans-dienoic acid methyl ester,
  8R-9-keto-11a-propionamidomethyl-15a-hydroxyprosta-5-cis,13-trans-dienoic acid methyl ester,
  8R-9-keto-11a-acetamidomethyl-15a-hydroxy-prost-13-trans-enoic acid methyl ester
  8R-9-keto-11a-formamidomethyl-15a-hydroxyprosta-5-cis,13-trans-dienoic acid methyl ester,
  8R-9-keto-11a-formamidomethyl-15a-hydroxyprost-13-trans-enoic acid methyl ester,
  8R-9-keto-11a-methoxymethyl-15a-hydroxy-prosta-5-cis,13-trans-dienoic acid methyl ester,
  8R-9-keto-11a-isopropoxymethyl-15a-hydroxyprosta-5-cis,13-trans-dienoic acid methyl ester,
  8R-9-keto-11a-methoxymethyl-15a-hydroxy-prost-13-trans-enoic acid methyl ester,
  8R-9-keto-11a-methylthiomethyl-15a-hydroxyprosta-5-cis,13-trans-dienoic acid methyl ester,
  8R-9-keto-11a-methylthiomethyl-15a-hydroxyprost-13-trans-enoic acid methyl ester,
  8R-9-keto-11a-methylsulfinylmethyl-15a-hydroxyprosta-5-cis,13-trans-dienoic acid methyl ester,
  8R-9-keto-11a-methylsulfinylmethyl-15a-hydroxyprost-13-trans-enoic acid methyl ester,
  8R-9-keto-11a-methylsulfonylmethyl-15a-hydroxyprosta-5-cis,13-trans-dienoic acid methyl ester,
  8R-9-keto-11a-methylsulfonylmethyl-15a-hydroxyprost-13-trans-enoic acid methyl ester,
  8R-9-keto-11a-N,N-dimethylaminomethyl-15a-hydroxyprosta-5-cis,13-trans-dienoic acid methyl ester,
  8R-9-keto-11a-N,N-dimethylaminomethyl-15a-hydroxyprost-13-trans-enoic acid methyl ester,
  8R-9-keto-11a-N-methyl-N-ethylaminomethyl-15a-hydroxyprosta-5-cis,13-trans-dienoic acid methyl ester,
  8R-9-keto-11a-N,N-dipropylaminomethyl-15a-hydroxyprost-13-trans-enoic acid methyl ester,
  8R-9-keto-11a-N-methylaminomethyl-15a-hydroxyprosta-5-cis,13-trans-dienoic acid methyl ester,
  8R-9-keto-11a-N-ethylaminomethyl-15a-hydroxyprost-13-trans-enoic acid methyl ester, and
  8R-9-keto-11a-N-t-butylaminomethyl-15a-hydroxyprosta-5-cis,13-trans-dienoic acid methyl ester, as well as the corresponding racemic compounds.

EXAMPLE 23

To a stirred solution of 100 mg. of 8R-9-keto-11a-chloromethyl-15a-hydroxyprosta-5-cis,13-trans-dienoic acid methyl ester in 5 ml. of dimethoxyethane, freshly distilled from lithium aluminum hydride is added 1 ml. of zinc borohydride reagent in anhydrous dimethoxyethane. The reaction mixture is stirred for an additional hour at room temperature, and treated with a saturated solution of sodium bitartrate until the evolution of gas ceases. It is then diluted with methylene chloride, and the organic layer separated, dried over magnesium sulfate and evaporated to dryness under vacuo at low temperature, to yield 8R-11q-black 13 chloromethyl-9a,15a-dihydroxyprosta-5-cis,13-trans-dienoic acid methyl ester in mixture with the 9β-hydroxy isomer (8R-antimers of XIV, $R^{6'}$ = Me; X = Cl; Z = double bond).

This oily mixture is separated into the individual isomers by thin-layer chromatography using a mixture of methylene chloride-methanol (9:1) as eluant.

The zinc borohydride reagent is prepared from 0.025 mol of fused zinc chloride, 0.050 mol of sodium borohydride in 50 ml. of dimethoxyethane, stirring the mixture for 16 hours and filtering the insoluble material under argon atmosphere.

By the same method from the corresponding 9-keto compounds there are obtained:
  8R-11a-bromomethyl-9a-,15a-dihydroxy-prosta-5-cis,13-trans-dienoic acid methyl ester and 8R-11a-bromomethyl-9β,15a-dihydroxyprosta-5-cis,13-trans-dienoic acid methyl ester;
  8R-11a-chloromethyl-9a,15a-dihydroxyprost-13-trans-enoic acid methyl ester and 8R-11a-chloromethyl-9β,15a-dihydroxyprost-13-trans-enoic acid methyl ester;
  8R-11a-bromomethyl-9a,15a-dihydroxyprost-13-trans-enoic acid methyl ester and 8R-11a-bromomethyl-9β,15a-dihydroxyprost-13-trans-enoic acid methyl ester,
  11a-chloromethyl-9a,15a-dihydroxyprosta-5-cis,13-trans-dienoic methyl ester and 11a-chloromethyl-9β,15α-dihydroxyprosta-5-cis,13-trans-dienoic acid methyl ester;
  11a-bromomethyl-9a,15a-dihydroxyprosta-5-cis,13-trans-dienoic acid methyl ester and 11a-bromomethyl-9β,15α-dihydroxyprosta-5-cis,13-trans-dienoic acid methyl ester;
  11a-chloromethyl-9a,15a-dihydroxyprost-13-trans-enoic acid methyl ester and 11a-chloromethyl-9β,15α-dihydroxyprost13-trans-enoic acid methyl ester; and
  11a-bromomethyl-9a,15a-dihydroxyprost-13-trans-enoic acid methyl ester and 11a-bromomethyl-9β,15α-dihydroxyprost-13-trans-enoic acid methyl ester.

EXAMPLE 24

To a solution of 200 mg. of 8R-9-keto-11α-azidomethyl-15α-hydroxyprosta-5-cis,13-trans-dienoic acid methyl ester in 5 ml. of methanol, cooled to 0°C is added 20 mg. of sodium borohydride, and the reaction mixture is stirred at 0°C for 45 minutes. It is then poured into water and extracted with ethyl acetate. The combined organic extracts are washed with 50% saturated sodium chloride solution, dried over sodium sulfate and evaporated to dryness under reduced pressure. The oily residue is dissolved in methylene chloride and purified by chromatography on Florisil. Those fractions eluted with methylene chloride-methanol (98:2) afford the pure, separated isomers, 8R-11α-azidomethyl-9α,15α-dihydroxyprosta-5-cis,13-trans-dienoic acid methyl ester and 8R-11α-azidomethyl-9β,15α-dihydroxyprosta-5-cis,13-trans-dienoic acid methyl ester (8R-antimers of XIV, $R^{6'}$ = Me; X = $N_3$; Z = double bond).

In a similar manner, the 9-keto compounds obtained in Example 22 are converted into the corresponding 9-hydroxy derivatives, namely:

8R-11α-aminomethyl-9α,15α-dihydroxyprosta-5-cis,13-trans-dienoic acid methyl ester and 8R-11α-aminomethyl-9β,15α-dihydroxyprosta-5-cis,13-trans-dienoic acid methyl ester;

8R-11α-aminomethyl-9α,15α-dihydroxyprost-13-trans-enoic acid methyl ester and 8R-11α-aminomethyl-9β,15α-dihydroxyprost-13-trans-enoic acid methyl ester;

8R-11α-acetamidomethyl-9α,15α-dihydroxyprosta-5-cis,13-trans-dienoic acid methyl ester and 8R-11α-acetamidomethyl-9β,15α-dihydroxyprosta-5-cis,13-trans-dienoic acid methyl ester;

8R-11α-propionamidomethyl-9α,15α-dihydroxyprosta-5-cis,13-trans-dienoic acid methyl ester and 8R-11α-propionamidomethyl-9β,15α-dihydroxyprosta-5-cis,13-trans-dienoic acid methyl ester;

8R-11α-acetamidomethyl-9α,15α-dihydroxyprost-13-trans-enoic acid methyl ester and 8R-11α-acetamidomethyl-9β,15α-dihydroxyprost-13-trans-enoic acid methyl ester;

8R-11α-formamidomethyl-9α,15α-dihydroxyprosta-5-cis,13-trans-dienoic acid methyl ester and 8R-11α-formamidomethyl-9β,15α-dihydroxyprosta-5-cis,13-trans-dienoic acid methyl ester;

8R-11α-formamidomethyl-9α,15α-dihydroxyprost-13-trans-enoic acid methyl ester and 8R-11α-formamidomethyl-9β,15α-dihydroxyprost-13-trans-enoic acid methyl ester;

8R-11α-methoxymethyl-9α,15α-dihydroxyprosta-5-cis,13-trans-dienoic acid methyl ester and 8R-11α-methoxymethyl-9β,15α-dihydroxyprosta-5-cis,13-trans-dienoic acid methyl ester;

8R-11α-isopropoxymethyl-9α,15α-dihydroxyprosta-5-cis,13-trans-dienoic acid methyl ester and 8R-11α-isopropoxymethyl-9β,15α-dihydroxyprosta-5-cis,13-trans-dienoic acid methyl ester;

8R-11α-methoxymethyl-9α,15α-dihydroxyprost-13-trans-enoic acid methyl ester and 8R-11α-methoxymethyl-9β,15α-dihydroxyprost-13-trans-enoic acid methyl ester;

8R-11α-methylthiomethyl-9α,15α-dihydroxyprosta-5-cis,13-trans-dienoic acid methyl ester and 8R-11α-methylthiomethyl-9β,15α-dihydroxyprosta-5-cis,13-trans-dienoic acid methyl ester;

8R-11α-methylthiomethyl-9α,15α-dihydroxyprost-13-trans-enoic acid methyl ester and 8R-11α-methylthiomethyl-9β,15α-dihydroxyprost-13-trans-enoic acid methyl ester;

8R-11α-methylsulfinylmethyl-9α,15α-dihydroxyprosta-5-cis,13-trans-dienoic acid methyl ester and 8R-11α-methylsulfinylmethyl-9β,15α-dihydroxyprosta-5-cis,13-trans-dienoic acid methyl ester;

8R-11α-methylsulfinylmethyl-9α,15α-dihydroxyprost-13-trans-enoic acid methyl ester and 8R-11α-methylsulfinylmethyl-9β,15α-dihydroxyprost-13trans-enoic acid methyl ester;

8R-11α-methylsulfonylmethyl-9α,15α-dihydroxyprosta-5-cis,13-trans-dienoic acid methyl ester and 8R-11α-methylsulfonylmethyl-9β,15α-dihydroxyprosta-5-cis,13-trans-dienoic acid methyl ester;

8R-11α-methylsulfonylmethyl-9α,15α-dihydroxyprost-13-trans-enoic acid methyl ester and 8R-11α-methylsulfonylmethyl-9β,15α-dihydroxyprost-13-trans-enoic acid methyl ester;

8R-11α-N,N-dimethylaminomethyl-9α,15α-dihydroxyprosta-5-cis,13-trans-dienoic acid methyl ester and 8R-11α-N,N-dimethylaminomethyl-9β,15α-dihydroxyprosta-5-cis,13-trans-dienoic acid methyl ester; 8R-11α-N,N-dimethylaminomethyl-9α,15α-dihydroxyprost-13-trans-enoic acid methyl ester and 8R-11α-N,N-dimethylaminomethyl-9β,15α-dihydroxyprost-13-trans-enoic acid methyl ester;

8R-11α-N-methyl-N-ethylaminomethyl-9α,15α-dihydroxyprosta-5-cis,13-trans-dienoic acid methyl ester and 8R-11α-N-methyl-N-ethylaminomethyl-9β,15α-dihydroxyprosta-5-cis,13-trans-dienoic acid methyl ester;

8R-11α-N,N-dipropylaminomethyl-9α,15α-dihydroxyprost-13-trans-enoic acid methyl ester and 8R-11α-N,N-dipropylaminomethyl-9β,15α-dihydroxyprost-13-trans-enoic acid methyl ester;

8R-11α-N-methylaminomethyl-9α,15α-dihydroxyprosta-5-cis,13-trans-dienoic acid methyl ester and 8R-11α-N-methylaminomethyl-9β,15α-dihydroxyprosta-5-cis,13-trans-dienoic acid methyl ester;

8R-11α-N-ethylaminomethyl-9α,15α-dihydroxyprost-13-trans-enoic acid methyl ester and 8R-11α-N-ethylaminomethyl-9β,15α-dihydroxyprost-13-trans-enoic acid methyl ester and 8R-11α-N-t-butylaminomethyl-9α,15α-dihydroxyprosta-5-cis,13-trans-dienoic acid methyl ester and 8R-11α-N-t-butylaminomethyl-9β,15α-dihydroxyprosta-5-cis,13-trans-dienoic acid methyl ester, as well as the corresponding racemic compounds.

Alternatively, the reduction of the 9-keto group can be carried out with zinc borohydride, in accordance with the method of Example 23.

EXAMPLE 25

A mixture of 250 mg. of 8R-9-keto-11α-hydroxymethyl-15α-acetoxyprosta-5-cis,13-trans-dienoic acid methyl ester, 10 ml. of 2-methyl-2-ethyl-1,3-dioxolane and 25 mg. of p-toluenesulfonic acid is heated to boiling and refluxed with distillation for 1 hour. It is then cooled, diluted with water and extracted with ethyl acetate. The organic extract is washed with sodium bicarbonate solution and sodium chloride solution, dried over sodium sulfate and evaporated to dryness under reduced pressure in the presence of a drop of pyridine, to afford 9-ethylenedioxy-11α-hydroxymethyl-15α-acetoxyprosta-5-cis,13-trans-dienoic acid methyl ester, which can be purified by t.l.c.

A mixture of 220 mg. of 9-ethylenedioxy-11α-hydroxymethyl-15α-acetoxyprosta-5-cis,13-trans-dienoic acid methyl ester, 450 mg. of methyltriphenoxyphosphonium iodide [prepared as described by J. P. H. Verheyden et al, in *J. Org. Chem.* 35, 2319 (1970)] and 5 ml. of anhydrous dimethylformamide is stirred at room temperature for 15 minutes. To the reaction mixture is added 0.5 ml. of methanol, after 10 minutes the solvent is evaporated under vacuo and the residue dissolved in methylene chloride. The organic solution is washed with aqueous sodium thiosulfate solution and water, dried over sodium sulfate and evaporated to dryness under reduced pressure. The residue is purified by t.l.c., to yield the pure 8R-9-ethylenedioxy-11α-iodomethyl-15α-acetoxyprosta-5-cis,13-trans-dienoic acid methyl ester.

To a solution of 100 mg. of 8R-9-ethylenedioxy-11α-iodomethyl-15α-acetoxyprosta-5-cis,13-trans-dienoic acid methyl ester in 5 ml. of acetonitrile is added a suspension of 50 mg. of silver fluoride in 0.2 ml. of water and 0.6 ml. of acetonitrile and the resulting mixture is stirred for 6 hours at 30°–40°C, the precipitate is filtered and the filtrate is concentrated to a small volume under reduced pressure. Water is then added and the product extracted with methylene chloride. The organic extract is dried over sodium sulfate and evaporated to dryness under reduced pressure. The residue is purifed by t.l.c. to afford 8R-9-ethylenedioxy-11α-fluoromethyl-15α-acetoxyprosta-5-cis,13-trans-dienoic acid methyl ester.

To a solution of 100 mg. of 8R-9-ethylenedioxy-11α-fluoromethyl-15α-acetoxyprosta-5-cis,13-trans-dienoic acid methyl ester in 5 ml. of tetrahydrofuran is added 1 ml. of 50% acetic acid, and the reaction mixture is maintained at room temperature for 24 hours. It is then evaporated to dryness under vacuo and the residue dissolved in ethyl acetate. The organic solution is washed with sodium bicarbonate solution and water, dried over sodium sulfate and evaporated to dryness under reduced pressure. The residue is purified by t.l.c. to afford 8R-9-keto-11α-fluoromethyl-15α-acetoxyprosta-5-cis,13-trans-dienoic acid methyl ester (8R-antimer of IV, $R^{6'}$ = Me; $R^7$ = Ac; Z = double bond).

In a similar manner but using 8R-9-keto-11α-hydroxymethyl-15α-acetoxyprost-13-trans-enoic acid methyl ester, 9-keto-11α-hydroxymethyl-15α-acetoxyprosta-5-cis,13-trans-dienoic acid methyl ester and 9-keto-11α-hydroxymethyl-15α-acetoxyprost-13-trans-enoic acid methyl ester in place of 8R-9-keto-11α-hydroxymethyl-15α-acetoxyprosta-5-cis,13-trans-dienoic acid methyl ester there are obtained as final products:

8R-9-keto-11α-fluoromethyl-15α-acetoxyprost-13-trans-enoic acid methyl ester;

9-keto-11α-fluoromethyl-15α-acetoxyprosta-5-cis,13-trans-dienoic acid methyl ester and 9-keto-11α-fluoromethyl-15α-acetoxyprost-13-trans-enoic acid methyl ester, respectively.

EXAMPLE 26

By following the method of Example 21, the 11α-fluoromethyl-15α-acetoxy compounds obtained in Example 25 are converted into the corresponding 15α-hydroxy derivatives, namely:

8R-9-keto-11α-fluoromethyl-15α-hydroxyprosta-5-cis,13-trans-dienoic acid methyl ester, 8R-keto-11α-fluoromethyl-15α-hydroxyprost-13-trans-enoic acid methyl ester, 9-keto-11α-fluoromethyl-15α-hydroxyprosta-5-cis,13-trans-dienoic acid methyl ester, and 9-keto-11α-fluoromethyl-15α-hydroxyprost-13-trans-enoic acid methyl ester.

Upon reduction of the 9-keto group, in accordance with the method of Example 23, there are respectively obtained:

8R-11α-fluoromethyl-9α,15α-dihydroxyprosta-5-cis,13-trans-dienoic acid methyl ester and 8R-11α-fluoromethyl-9β,15α-dihydroxyprosta-5-cis,13-dienoic acid methyl ester;

8R-11α-fluoromethyl-9α,15α-dihydroxyprost-13-trans-enoic acid methyl ester and 8R-11α-fluoromethyl-9β,15α-dihydroxyprost-13-trans-enoic acid methyl ester;

11α-fluoromethyl-9α,15α-dihydroxyprosta-5-cis,13-trans-dienoic acid methyl ester and 11α-fluoromethyl-9β,15α-dihydroxyprosta-5-cis,13-trans-dienoic acid methyl ester; and 11α-fluoromethyl-9α,15α-dihydroxyprost-13-trans-enoic acid methyl ester and 11α-fluoromethyl-9β,15α-dihydroxyprost-13-trans-enoic acid methyl ester.

EXAMPLE 27

A. A mixture of 200 mg. of 8R-11α-fluoromethyl-9α,15α-dihydroxyprosta-5-cis,13-trans-dienoic acid methyl ester, 10 ml. of dioxane and 400 mg. of 2,3-dichloro-5,6-dicyano-1,4-benzoquinone is stirred at 50°C to 55°C for 18 hours. The reaction mixture is then evaporated to dryness under reduced pressure and the residue is dissolved in methylene chloride and chromatographed on Florisil. The fractions eluted with methylene chloride-ether (9:1) afford 8R-9α-hydroxy-11α-fluoromethyl-15-ketoprosta-5-cis,13-trans-dienoic acid methyl ester in pure form (8R-antimer of XV, X = F; Z = double bond).

B. A solution of 230 mg. of 8R-9α-hydroxy-11α-fluoromethyl-15-ketoprosta-5-cis,13-trans-dienoic acid methyl ester in 20 ml. of anhydrous ether is cooled to −20°C and treated dropwise, under stirring and under argon atmosphere with 6 molar equivalents of a 3N methylmagnesium bromide solution in ether. The temperature of the reaction mixture is allowed to rise to −5°C, 6 additional molar equivalents of methylmagnesium bromide solution are added, and the resulting mixture is stirred for 1 hour more, at the end of which time there are added 5 ml. of methanol. The resulting mixture is diluted with water and ethyl acetate, and the insoluble material filtered through Celite, diatomaceous earth. The organic phase is separated from the filtrate and washed with saturated sodium chloride solution, dried over magnesium sulfate and evaporated to dryness under reduced pressure. The oily residue is purified by thin layer chromatography, to produce the pure 8R-11α-fluoromethyl-15β-methyl-9α,15α-dihydroxyprosta-5-cis,13-trans-dienoic acid methyl ester and 8R-11α-fluoromethyl-15α-methyl-9α,15β-dihydroxyprosta-5-cis,13-trans-dienoic acid methyl ester in approximately equal amounts [8R-antimer of XVI ($R^2$ and $R^{6'}$ = Me; X = F; Z = double bond)].

In a similar manner but using ethylmagnesium bromide in place of methylmagnesium bromide there are obtained 8R-11α-fluoromethyl-15β-ethyl-9α,15α-dihydroxyprosta-5-cis,13-trans-dienoic acid methyl ester and the 15α-ethyl-15β-hydroxy isomer.

EXAMPLE 28

Example 27 is repeated using as starting materials the 8R-antimeric and racemic compounds obtained in Examples 23 and 24. Representative compounds thus obtained are:

8R-11α-bromomethyl-15ξ-methyl-9α,15ξ-dihydroxyprosta-5-cis,13-trans-dienoic acid methyl ester,
8R-11α-bromomethyl-15ξ-methyl-9β,15ξ-dihydroxyprost-13-trans-enoic acid methyl ester,
8R-11α-chloromethyl-15ξ-methyl-9α,15ξ-dihydroxyprosta-5-cis,13-trans-dienoic acid methyl ester,
8R-11α-azidomethyl-15ξ-methyl-9α,15ξ-dihydroxyprosta-5-cis,13-trans-dienoic acid methyl ester,
8R-11α-aminomethyl-15ξ-methyl-9α,15ξ-dihydroxyprosta-5-cis,13-trans-dienoic acid methyl ester,
8R-11α-aminomethyl-15ξ-methyl-9α,15ξ-dihydroxyprost-13-trans-enoic acid methyl ester,
8R-11α-acetamidomethyl-15ξ-methyl-9α,15ξ-dihydroxyprosta-5-cis,13-trans-dienoic acid methyl ester,
8R-11α-formamidomethyl-15ξ-methyl-9α,15ξ-dihydroxyprosta-5-cis,13-trans-dienoic acid methyl ester,
8R-11α-formamidomethyl-15ξ-methyl-9α,15ξ-dihydroxyprost-13-trans-enoic acid methyl ester,
8R-11α-methoxymethyl-15ξ-methyl-9α,15ξ-dihydroxyprosta-5-cis,13-trans-dienoic acid methyl ester,
8R-11α-methoxymethyl-15ξ-methyl-9β,15ξ-dihydroxyprost-13-trans-enoic acid methyl ester,
8R-11α-methylthiomethyl-15ξ-methyl-9α,15ξ-dihydroxyprosta-5-cis,13-trans-dienoic acid methyl ester,
8R-11α-methylthiomethyl-15ξ-methyl-9β,15ξ-dihydroxyprost-13-trans-enoic acid methyl ester,
8R-11α-methylsulfinylmethyl-15ξ-methyl-9α,15ξ-dihydroxyprosta-5-cis,13-trans-dienoic acid methyl ester,
8R-11α-methylsulfonylmethyl-15ξ-methyl-9α,15ξ-dihydroxyprosta-5-cis,13-trans-dienoic acid methyl ester,
8R-11α-methylsulfonylmethyl-15ξ-methyl-9β,15ξ-dihydroxyprost-13-trans-enoic acid methyl ester,
8R-11α-N,N-dimethylaminomethyl-15ξ-methyl-9α,15ξ-dihydroxyprosta-5-cis,13-trans-dienoic acid methyl ester,
8R-11α-N-methylaminomethyl-15ξ-methyl-9α,15ξ-dihydroxyprosta-5-cis,13-trans-dienoic acid methyl ester,
8R-11α-N-ethylaminomethyl-15ξ-methyl-9β,15ξ-dihydroxyprost-13-trans-enoic acid methyl ester,
11α-fluoromethyl-15ξ-methyl-9α,15ξ-dihydroxyprosta-5-cis,13-trans-dienoic acid methyl ester,
11α-chloromethyl-15ξ-methyl-9β,15ξ-dihydroxyprosta-5-cis,13-trans-dienoic acid methyl ester,
11α-azidomethyl-15ξ-methyl-9α,15ξ-dihydroxyprosta-5-cis,13-trans-dienoic acid methyl ester,
11α-aminomethyl-15ξ-methyl-9β,15ξ-dihydroxyprosta-5-cis,13-trans-dienoic acid methyl ester,
11α-methoxymethyl-15ξ-methyl-9α,15ξ-dihydroxyprost-13-trans-enoic acid methyl ester,
11α-methylthiomethyl-15ξ-methyl-9α,15ξ-dihydroxyprosta-5-cis,13-trans-dienoic acid methyl ester and
11α-N,N-dimethylaminomethyl-15ξ-methyl-9α,15ξ-dihydroxyprosta-5-cis,13-trans-dienoic acid methyl ester, separating the individual 15α-hydroxy-15β-methyl- and 15β-hydroxy-15α-methyl isomers by thin layer chromatography.

When using ethylmagnesium bromide in place of methylmagnesium bromide in the procedure of part B of Example 27 there are obtained the 15ξ-hydroxy-15ξ-ethyl derivatives of the above-mentioned compounds.

EXAMPLE 29

To a suspension of 2 g. of Celite, diatomaceous earth (dried for 24 hours at 105°C) and 1 g. of chromium trioxide-dipyridine complex, [prepared as described by J. C. Collins et al., in *Tetrahedron Letters*, 3363 (1968)] in 15 ml. of methylene chloride, cooled to −5°C is added, with stirring, a solution of 130 mg. of 8R-11α-fluoromethyl-15β-methyl-9α,15α-dihydroxyprosta-5-cis,13-trans-dienoic acid methyl ester in 5 ml. of methylene chloride and the mixture is stirred for 15 minutes further at 0°–5°C; 300 mg. of sodium bisulfate monohydrate are then added and the reaction mixture is stirred for an additional 10 minute period. The insoluble material is separated by filtration and washed well with methylene chloride. The combined organic filtrates are evaporated to dryness under vacuo and the residue purified by thin layer chromatography, thus obtaining 8R-9-keto-11α-fluoromethyl-15β-methyl-15α-hydroxyprosta-5-cis,13-trans-dienoic acid methyl ester (8R-antimer of XVII, $R^2$ and $R^{6'}$ = Me; X = F; Z = double bond) in pure form.

In a similar manner, starting from the corresponding 9α-(or 9β) hydroxy compounds obtained in Example 28, there are produced:

8R-9-keto-11α-bromomethyl-15β-methyl-15α-hydroxyprosta-5-cis,13-trans-dienoic acid methyl ester,
8R-9-keto-11α-bromomethyl-15β-methyl-15α-hydroxyprost-13-trans-enoic acid methyl ester,
8R-9-keto-11α-chloromethyl-15β-methyl-15α-hydroxyprosta-5-cis,13-trans-dienoic acid methyl ester,
8R-9-keto-11α-azidomethyl-15β-methyl-15α-hydroxyprosta-5-cis,13-trans-dienoic acid methyl ester,
8R-9-keto-11α-aminomethyl-15β-methyl-15α-hydroxyprosta-5-cis,13-trans-dienoic acid methyl ester,
8R-9-keto-11α-acetamidomethyl-15β-methyl-15α-hydroxyprosta-5-cis,13-trans-dienoic acid methyl ester,
8R-9-keto-11α-formamidomethyl-15β-methyl-15α-hydroxyprost-13-trans-enoic acid methyl ester,
8R-9-keto-11α-methoxymethyl-15β-methyl-15α-hydroxyprosta-5-cis,13-trans-dienoic acid methyl ester,
8R-9-keto-11α-methoxymethyl-15β-methyl-15α-hydroxyprost-13-trans-enoic acid methyl ester,
8R-9-keto-11α-methylthiomethyl-15β-methyl-15α-hydroxyprosta-5-cis,13-trans-dienoic acid methyl ester,
8R-9-keto-11α-methylsulfinylmethyl-15β-methyl-15α-hydroxyprosta-5-cis,13-trans-dienoic acid methyl ester,
8R-9-keto-11α-methylsulfonylmethyl-15β-methyl-15α-hydroxyprosta-5-cis,13-trans-dienoic acid methyl ester,
8R-9-keto-11α-methylsulfonylmethyl-15β-methyl-15α-hydroxyprost-13-trans-enoic acid methyl ester,
8R-9-keto-11α-N,N-dimethylaminomethyl-15β-methyl-15α-hydroxyprosta-5-cis,13-trans-dienoic acid methyl ester,
8R-9-keto-11α-N-methylaminomethyl-15β-methyl-15α-hydroxyprosta-5-cis,13-trans-dienoic acid methyl ester,
8R-9-keto-11α-N-ethylaminomethyl-15β-methyl-15α-hydroxyprost-13-trans-enoic acid methyl ester,
9-keto-11α-fluoromethyl-15β-methyl-15α-hydroxyprosta-5-cis,13-trans-dienoic acid methyl ester,
9-keto-11α-chloromethyl-15β-methyl-15α-hydroxyprosta-5-cis,13-trans-dienoic acid methyl ester,
9-keto-11α-azidomethyl-15β-methyl-15α-hydroxyprosta-5-cis,13-trans-dienoic acid methyl ester,
9-keto-11α-aminomethyl-15β-methyl-15α-hydroxyprosta-5-cis,13-trans-dienoic acid methyl ester,
9-keto-11α-methoxymethyl-15β-methyl-15α-hydroxyprost-13-trans-enoic acid methyl ester,
9-keto-11α-methylthiomethyl-15β-methyl-15α-hydroxyprosta-5-cis,13-trans-dienoic acid methyl ester, and
9-keto-11α-N,N-dimethylaminomethyl-15β-methyl-15α-hydroxyprosta-5-cis,13-trans-dienoic acid methyl ester, as well as the corresponding 15α-methyl-15β-hydroxy isomers and the 15-ethyl derivatives thereof.

EXAMPLE 30

A. A suspension of 5 g. of crude pancreatic lipase (Sigma L-3126) in 40 ml. of a 0.1M sodium chloride and 0.05M calcium chloride solution in water is stirred at 25°C for one hour. The mixture is then centrifuged for one hour at 5000 rev/min. and at 25° to 30°C. The supernatant is neutralized with 1N sodium hydroxide solution to pH 7.2 to 7.4 and used directly for the hydrolysis of the prostaglandin derivatives of the invention.

B. Forty-two milligrams of 8R-11α-fluoromethyl-9α,15α-dihydroxyprosta-5-cis,13-trans-dienoic acid methyl ester are dissolved by sonication at 37°C for 20 minutes in 30 ml. of the lipase solution prepared as described in part A. The reaction mixture is magnetically stirred for 24 hours at 25° to 26°C, adjusting constantly the pH at 7.2 to 7.4 during the reaction period with 0.1N sodium hydroxide solution. The cold reaction mixture is then acidified with 0.1N acetic acid solution and the product extracted several times from the solution with ethyl acetate and ether. The combined organic extracts are dried over sodium sulfate and evaporated to dryness under vacuo. The residue is dissolved in methylene chloride and chromatographed on 3 g. of Florisil. The column is eluted successively with methylene chloride-diethyl ether mixtures, diethyl ether, diethyl ether-ethyl acetate mixtures, pure ethyl acetate and ethyl acetate containing 1% methanol. The fractions eluted with the latter solvent mixture afford the pure 8R-11α-fluoromethyl-9α,15α-dihydroxyprosta-5-cis,13-trans-dienoic acid (8R-antimer of XIV, X = F; $R^{6'}$ = H; Z = double bond).

By the following the above procedure, from the corresponding methyl ester compounds obtained in Examples 23 and 26 there are produced:
8R-11α-bromomethyl-9α,15α-dihydroxyprosta-5-cis,13-trans-dienoic acid,
8R-11α-chloromethyl-9α,15α-dihydroxyprosta-5-cis,13-trans-dienoic acid,
8R-11α-fluoromethyl-9α,15α-dihydroxyprost-13-trans-enoic acid,
8R-11α-bromomethyl-9α,15α-dihydroxyprost-13-trans-enoic acid,
8R-11α-chloromethyl-9α,15α-dihydroxyprost-13-trans-enoic acid,
8R-9-keto-11α-fluoromethyl-15α-hydroxyprosta-5-cis,13-trans-dienoic acid,
8R-9-keto-11α-fluoromethyl-15α-hydroxyprost-13-trans-enoic acid,
9-keto-11α-fluoromethyl-15α-hydroxyprosta-5-cis,13-trans-dienoic acid,
11α-fluoromethyl-9α,15α-dihydroxyprosta-5-cis,13-trans-dienoic acid,
11α-bromomethyl-9α,15α-dihydroxyprosta-5-cis,13-trans-dienoic acid and
11α-chloromethyl-9α,15α-dihydroxyprosta-5-cis,13-trans-dienoic acid,
as well as the corresponding 9β-hydroxy isomers of the 9,15-dihydroxylated compounds.

EXAMPLE 31

To a solution of 150 mg. of 8R-11α-azidomethyl-9α,15α-dihydroxyprosta-5-cis,13-trans-dienoic acid methyl ester in 10 ml. of methanol is added to a solution of 150 mg. of potassium carbonate in 1 ml. of water, under nitrogen atmosphere. The reaction mixture is kept at room temperature for 18 hours. It is then poured into ice water and extracted with methylene chloride, the organic extract is discharged and the aqueous phase is cooled to 0°C, acidified with 0.1N hydrochloric acid and extracted several times with methylene chloride. The combined organic extracts are washed with saturated sodium chloride solution, dried over sodium sulfate and evaporated to dryness under reduced pressure. Purification of the residue by thin layer chromatography affords the pure 8R-11α-azidomethyl-9α,15α-dihydroxyprosta-5-cis,13-trans-dienoic acid, (8R-antimer of XIV, X = $N_3$; $R^{6'}$ = H; Z = double bond).

By following the above procedure or the procedure of Example 30, from the corresponding methyl ester compounds obtained as described in Example 24 there are produced the following prostadienoic and prostenoic acids:
8R-11α-acetamidomethyl-9α,15α-dihydroxyprosta-5-cis,13-trans-dienoic acid,
8R-11α-acetamidomethyl-9α,15α-dihydroxyprost-13-trans-enoic acid,
8R-11α-formamidomethyl-9α,15α-dihydroxyprosta-5-cis,13-trans-dienoic acid,
8R-11α-formamidomethyl-9α,15α-dihydroxyprost-13-trans-enoic acid,
8R-11α-methoxymethyl-9α,15α-dihydroxyprosta-5-cis,13-trans-dienoic acid,
8R-11α-isopropoxymethyl-9α,15α-dihydroxyprosta-5-cis,13-trans-dienoic acid,
8R-11α-methoxymethyl-9α,15α-dihydroxyprost-13-trans-enoic acid,
8R-11α-methylthiomethyl-9α,15α-dihydroxyprosta-5-cis,13-trans-dienoic acid,
8R-11α-methylthiomethyl-9α,15α-dihydroxyprost-13-trans-enoic acid,
8R-11α-methylsulfinylmethyl-9α,15α-dihydroxyprosta-5-cis,13-trans-dienoic acid,
8R-11α-methylsulfinylmethyl-9α,15α-dihydroxyprost-13-trans-enoic acid, 8R-11α-methylsulfonylmethyl-9α,15α-dihydroxy-prosta-5-cis,13-trans-dienoic acid, and 8R-11α-methylsulfonylmethyl-9α,15α-dihydroxy-prost-13-trans-enoic acid, as well as the corresponding 9β-hydroxy isomers and the racemic compounds thereof.

EXAMPLE 32

To a solution of 200 mg. of 8R-9-keto-11α-N-methylaminomethyl-15α-hydroxyprosta-5-cis,13-trans-dienoic acid methyl ester in 15 ml. of methanol is added a solution of 200 mg. of potassium carbonate in 2 ml. of water, under nitrogen atmosphere and the reaction mixture is maintained at room temperature for 16 hours. The solvent is then eliminated under reduced pressure and the residue is dissolved in 20 ml. of water and passed through a column of 5 g. of ion exchange resin "Dowex" 50, acidic type ($H^+$) eluting the column first with water and thereafter with 10% acetic acid solution. The combined acidic eluates are concentrated to a small volume under reduced pressure at low temperature and then lyophilized, to yield 8R-9-keto-11α-N-methylaminomethyl-15α-hydroxyprosta-5-cis,13-trans-dienoic acid (8R-antimer of XII, $R^4$ = Me; $R^5$ and $R^{6'}$ = H; Z = double bond).

By the same method, from the corresponding methyl ester derivatives there are obtained:

8R-9-keto-11α-N,N-dimethylaminomethyl-15α-hydroxyprosta-5-cis,13-trans-dienoic acid, 8R-9-keto-11α-N-ethylaminomethyl-15α-hydroxyprost-13-trans-enoic acid, 8R-11α-aminomethyl-9α,15α-dihydroxyprosta-5-cis,13-trans-dienoic acid, 8R-11α-N-methylaminomethyl-9α,15α-dihydroxyprosta-5-cis,13-trans-dienoic acid, 8R-11α-N,N-dimethylaminomethyl-9α,15α-dihydroxyprosta-5-cis,13-trans-dienoic acid, 8R-11α-N,N-dimethylaminomethyl-9α,15α-dihydroxyprost-13-trans-enoic acid, 8R-11α-aminomethyl-9α,15α-dihydroxyprost-13-trans-enoic acid, 8R-11α-aminomethyl-15β-methyl-9α,15α-dihydroxyprosta-5-cis,13-trans-dienoic acid, 8R-11α-N-methylaminomethyl-15β-methyl-9α,15α-dihydroxyprosta-5-cis,13-trans-dienoic acid, 8R-11α-N,N-dimethylaminomethyl-15β-methyl-9α,15α-dihydroxyprosta-5-cis,13-trans-dienoic acid, 8R-11α-aminomethyl-15β-methyl-9α,15α-dihydroxyprost-13-trans-enoic acid, 8R-9-keto-11α-aminomethyl-15β-methyl-15α-hydroxyprosta-5-cis,13-trans-dienoic acid, and 8R-9-keto-11α-N,N-dimethylaminomethyl-15β-methyl-15α-hydroxyprosta-5-cis,13-trans-dienoic acid, as well as the corresponding racemic compounds.

EXAMPLE 33

To a solution of 110 mg. of 8R-9-keto-11α-azidomethyl-15β-methyl-15α-hydroxyprosta-5-cis,13-trans-dienoic acid methyl ester in 3 ml. of methanol are added 165 mg. of potassium carbonate and 0.66 ml. of water, under nitrogen atmosphere and the reaction mixture is kept at room temperature for 16 hours. It is then evaporated to dryness under vacuo and the oily residue taken up in 10 ml. of water and 10 ml. of methylene chloride. The aqueous phase is separated and the organic phase which contains the unsaponifiable products is washed with saturated sodium potassium tartrate solution. The combined aqueous phases are saturated with sodium potassium tartrate, cooled to 0°C and treated dropwise with 0.1N acetic acid solution. It is then extracted three times with cold ethyl acetate and the combined organic extracts washed with saturated sodium potassium tartrate solution, dried and evaporated to dryness. The residue is purified by t.l.c., to afford the pure 8R-9-keto-11α-azidomethyl-15β-methyl-15α-hydroxyprosta-5-cis,13-trans-dienoic acid (8R-antimer of XVII, $R^2$ = Me; $R^{6'}$ = H; X = $N_3$; Z = double bond).

EXAMPLE 34

A mixture of 90 mg. of 8R-9-keto-11α-azidomethyl-15β-methyl-15α-hydroxyprosta-5-cis,13-trans-dienoic acid methyl ester, 1.8 g. of dry finely ground freshly extracted residue of the gorgonian *Plexaura homomalla* (Esper), [which results after extraction of the prostaglandin derivatives contained originally by this gorgonian, as described by A. Prince et al., in *Prostaglandins*, Vol. 3, No. 4, p. 531 (1973)] and 10 ml. of 0.1M sodium chloride and 0.05M calcium chloride solution in water is stirred at room temperature for 24 hours, maintaining the pH of the reaction mixture at 7.5–7.7 by addition of 0.1N sodium hydroxide solution. At the end of this time the reaction mixture is diluted with 15 ml. of acetone, adjusting the pH to 4, with dilute acetic acid. Charcoal is added to decolorize the solution, and the insoluble material separated by filtration through Celite, diatomaceous earth, washing the solids with several portions of acetone. The combined filtrates are concentrated under reduced pressure to a small volume, and the product extracted from the aqueous residue with methylene chloride. The combined organic extracts are dried over magnesium sulfate and evaporated to dryness under reduced pressure. The oily residue is purified by t.l.c., thus obtaining the pure 8R-9-keto-11α,-azidomethyl-15β-methyl-15α-hydroxyprosta-5-cis,13-trans-dienoic acid, identical to the compound obtained in Example 33.

EXAMPLE 35

In accordance with the methods of Examples 30, 33 or 34, using the corresponding methyl ester prostadienoic and prostenoic acid derivatives as starting materials, there are produced the following representative free acids:

8R-11α-azidomethyl-15β-methyl-9α,15α-dihydroxyprosta-5-cis,13-trans-dienoic acid, 8R-11α-acetamidomethyl-15β-methyl-9α,15α-dihydroxyprosta-5-cis,13-trans-dienoic acid, 8R-11α-acetamidomethyl-15β-methyl-9α,15α-dihydroxyprost-13-trans-enoic acid, 8R-11α-formamidomethyl-15β-methyl-9α,15α-dihydroxyprosta-5-cis,13-trans-dienoic acid, 8R-11α-formamidomethyl-15β-ethyl-9α,15α-dihydroxyprost-13-trans-enoic acid, 8R-11α-methoxymethyl-15β-methyl-9α,15α-dihydroxyprosta-5-cis,13-trans-dienoic acid, 8R-11α-methylthiomethyl-15β-methyl-9α,15α-dihydroxyprosta-5-cis,13-trans-dienoic acid, 8R-11α-methylsulfinylmethyl-15β-methyl-9α,15α-dihydroxyprosta-5-cis,13-trans-dienoic acid, 8R-11α-methylsulfonylmethyl-15β-methyl-9α,15α-dihydroxyprosta-5-cis,13-trans-dienoic acid, 11α-azidomethyl-15β-methyl-9α,15α-dihydroxy-prosta-5-cis,13-trans-dienoic acid,
11α-methoxymethyl-15β-methyl-9α, 15α-dihydroxyprost-13-trans-enoic acid,
11α-methylthiomethyl-15β-methyl-9α,15α-dihydroxyprosta-5-cis,13-trans-dienoic acid,
8R-9-keto-11α-azidomethyl-15β-methyl-15α-hydroxyprost-13-trans-enoic acid,
8R-9-keto-11α-acetamidomethyl-15β-methyl-15α-hydroxyprosta-5-cis,13 -trans-dienoic acid,
8R-9-keto-11α-acetamidomethyl-15β-methyl-15α-hydroxyprost-13-trans-enoic acid,
8R-9-keto-11α-formamidomethyl-15β-methyl-15α-hydroxyprost-13-trans-enoic acid,
8R-9-keto-11α-methoxymethyl-15β-methyl-15α-hydroxyprosta-5-cis,13-trans-dienoic acid,
8R-9-keto-11α-methoxymethyl-15β-methyl-15α-hydroxyprost-13-trans-enoic acid,
8R-9-keto-11α-methylthiomethyl-15β-methyl-15α-hydroxyprosta-5-cis,13-trans-dienoic acid,
8R-9-keto-11α-methylsulfinylmethyl-15β-methyl-15α-hydroxyprosta-5-cis,13-trans-dienoic acid,
8R-9-keto-11α-methylsulfonylmethyl-15β-methyl-15α-hydroxyprosta-5-cis,13-trans-dienoic acid,
9-keto-11α-azidomethyl-15β-methyl-15α-hydroxyprosta-5-cis,13-trans-dienoic acid and
9-keto-11α-methoxymethyl-15β-methyl-15α-hydroxyprost-13-trans-enoic acid.

EXAMPLE 36

By following the method of Example 30
8R-11α-fluoromethyl-15β-methyl-9α,15α-dihydroxyprosta-5-cis,13-trans-dienoic acid methyl ester,
8R-11α-bromomethyl-15β-ethyl-9α,15α-dihydroxyprosta-5-cis,13-trans-dienoic acid methyl ester,
8R-11α-chloromethyl-15β-methyl-9α,15α-dihydroxyprosta-5-cis,13-trans-dienoic acid methyl ester,
8R-9-keto-11α-fluoromethyl-15β-methyl-15α-hydroxyprosta-5-cis,13-trans-dienoic acid methyl ester,
8R-9-keto-11α-chloromethyl-15β-ethyl-15α-hydroxyprosta-5-cis,13-trans-dienoic acid methyl ester,
8R-9-keto-11α-bromomethyl-15β-methyl-15α-hydroxyprosta-5-cis,13-trans-dienoic acid methyl ester and the corresponding racemic compounds are converted into the respective free acids.

EXAMPLE 37

To a solution of 100 mg. of 8R-9-keto-11α-chloromethyl-15α-hydroxyprosta-5-cis,13-trans-dienoic acid in 5 ml. of ether is added 1 ml. of an ethereal solution of diazoethane, and the reaction mixture is maintained at room temperature for 10 minutes. The solvents and excess reagent are eliminated by vacuum distillation and the residue is purified by t.l.c. to afford 8R-9-keto-11α-chloromethyl-15α-hydroxyprosta-5-cis,13-trans-dienoic acid ethyl ester.

In a similar manner but using diazopropane in place of diazoethane, the propyl ester of 8R-9-keto-11α-chloromethyl-15α-hydroxyprosta-5-cis,13-trans-dienoic acid is obtained.

By the same method the free 8R-antimeric and racemic prostadienoic and prostenoic acid derivatives obtained in Examples 20 and 30 to 36 can be converted into the corresponding ethyl and propyl esters.

EXAMPLE 38

To a solution of 100 mg. of 8R-9-keto-11α-azidomethyl-15α-hydroxyprosta-5-cis,13-trans-dienoic acid in 10 ml. of methanol is added 3.0 ml. of a 0.1N solution of sodium hydroxide and the mixture is stirred at room temperature for 1 hour. It is then evaporated to dryness under reduced pressure, to give the sodium salt of 8R-9-keto-11α-azidomethyl-15α-hydroxyprosta-5-cis,13-trans-dienoic acid.

By employing 1.1 molar equivalents of potassium hydroxide (in the form of a 0.1N solution) in place of sodium hydroxide in the above procedure the potassium salt of 8R-9-keto-11α-azidomethyl-15α-hydroxyprosta-5-cis,13-trans-dienoic acid is obtained.

Similarly, the sodium and potassium salts of other prostadienoic and prostenoic acid derivatives obtained in the previous Examples can be produced, e.g., sodium salt of 8R-9-keto-11α-azidomethyl-15α-hydroxyprost-13-trans-enoic acid,
sodium salt of 8R-11α-methoxymethyl-9α,15α-dihydroxyprosta-5-cis,13-trans-dienoic acid,
sodium salt of 8R-9-keto-11α-methylthiomethyl-15α-hydroxyprosta-5-cis,13-trans-dienoic acid,
potassium salt of 8R-9-keto-11α-methylsulfinylmethyl-15α-hydroxyprosta-5-cis,13-trans-dienoic acid,
potassium salt of 8R-11α-methylsulfonylmethyl-9α,15α-dihydroxyprosta-5-cis,15-trans-dienoic acid, and
potassium salt of 8R-11α-methoxymethyl-15β-methyl-9α,15α-dihydroxyprosta-5-cis,13-trans-dienoic acid.

EXAMPLE 39

To a solution of 100 mg. of 8R-11α-methoxymethyl-9α,15α-dihydroxyprosta-5-cis,13-trans-dienoic acid in 10 ml. of methanol is added a mixture of 3 ml. of concentrated ammonium hydroxide solution and 5 ml. of methanol. The resulting mixture is stirred for two hours at room temperature and then evaporated to dryness, to yield the ammonium salt of 8R-11α-methoxymethyl-9α,15α-dihydroxyprosta-5-cis,13-trans-dienoic acid.

By employing dimethylamine, diethylamine or dipropylamine in place of ammonium hydroxide in the above procedure, the corresponding salts of 8R-11α-methoxymethyl-9α,15α-dihydroxyprosta-5-cis,13-trans-dienoic acid are obtained.

In a similar manner, the ammonium, dimethylamine, diethylamine and dipropylamine salts of other prostadienoic and prostenoic acid derivatives of the previous Examples can be prepared.

EXAMPLE 40

To a mixture of 142 mg. of procaine and 5 ml. of aqueous methanol is added 100 mg. of 8R-9-keto-11α-azidomethyl-15α-hydroxyprosta-5-cis,13-trans-dienoic acid in 5 ml. of methanol and the resultant reaction mixture is stirred at room temperature for 16 hours. It is then evaporated to dryness under reduced pressure to give the procaine salt of 8R-9-keto-11α-azidomethyl-15α-hydroxyprosta-5-cis,13-trans-dienoic acid.

Similarly, the lysine caffeine and arginine salts thereof are obtained.

In like manner, the procaine, lysine, caffeine and arginine salts of other prostadienoic and prostenoic acid derivatives obtained in Examples 20 and 30 to 36 can be produced e.g., the procaine salt of 8R-11α- methoxymethyl-9α,15α-dihydroxyprosta-5-cis,13-trans-dienoic acid, the caffeine salt of 8R-9-keto-11α-methylthiomethyl-15α-hydroxyprosta-5-cis,13-trans-dienoic acid, the lysine salt of 8R-11α-fluoromethyl-15β-methyl-9α,15α-dihydroxyprosta-5-cis,13-trans-dienoic acid and the arginine salt of 8R-9-keto-11α-methylsulfonylmethyl-15α-hydroxyprost-13-trans-enoic acid, as well as the corresponding salts of the racemic compounds.

We claim:

1. An 8R-antimeric or racemic compound selected from the group of those represented by the formulas:

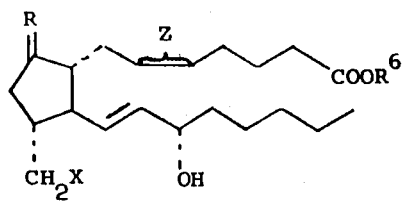

(A)

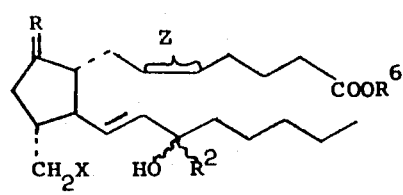

(B)

wherein
R is a keto group;
X is thiomethyl, methylsulfinyl

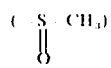

or methylsulfonyl

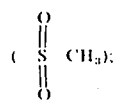

$R^2$ is methyl or ethyl;

$R^6$ is hydrogen, a lower alkyl group of 1 to 4 carbon atoms or the pharmaceutically acceptable, nontoxic salts of compounds in which $R^6$ is hydrogen, Z is a cis double bond and the wavy lines ( $\xi$ ) indicate the α or β configuration or mixtures thereof, provided that when $R^2$ is α, the hydroxyl group, attached to the same carbon atom as $R^2$, is β, and when $R^2$ is β, the hydroxyl group, attached to the same carbon atom as $R^2$, is α.

2. A compound according to claim 1 wherein $R^6$ is hydrogen.

3. A compound according to claim 1, formula (A), wherein said compound is an 8R-antimer.

4. A compound according to claim 1, formula (B) wherein said compound is an 8R-antimer.

5. A compound according to claim 3 wherein R is keto, X is methylsulfinyl, Z is a cis double bond and $R^6$ is hydrogen or methyl, 8R-9-keto-11α-methylsulfinylmethyl-15α-hydroxyprosta-5-cis,13-trans-dienoic acid and its methyl ester.

6. A compound according to claim 3 wherein R is keto, X is methylsulfonyl, Z is a cis double bond and $R^6$ is hydrogen or methyl; 8R-9-keto-11α-methylsulfonylmethyl-15α-hydroxyprosta-5-cis,13-trans-dienoic acid and its methyl ester.

7. A compound according to claim 3 wherein R is keto, X is thiomethyl, Z is a cis double bond and $R^6$ is hydrogen or methyl, 8R-9-keto-11α-methylthiomethyl-15α-hydroxyprosta-5-cis,13-trans-dienoic acid and its methyl ester.

* * * * *

UNITED STATES PATENT AND TRADEMARK OFFICE
CERTIFICATE OF CORRECTION

PATENT NO. : 3,935,241
DATED : January 27, 1976
INVENTOR(S) : JOSEPH M. MUCHOWSKI ET AL It is certified that error appears in the above-identified patent and that said Letters Patent are hereby corrected as shown below:

Column 2, line 57, "62" should read --- β ---.  Column 7, line 46, "obained" should read --- obtained ---.  Column 9, line 6, "tris(-dimethylamino)" should read --- tris(dimethylamino) ---.  Column 14, line 55, "15αhydroxy" should read --- 15α-hydroxy ---  Column 15, line 25, "10°" should read --- -10° ---.  Column 16, line 1, "of" should read --- by ---.  Column 20, line 6, "transenoic" should read --- trans-enoic ---.  Column 22, line 17, "mixtue" should read --- mixture ---.
Column 26, line 4, "-8° to 65°C." should read --- -58° to -65°C. ---.  Column 30, line 26, "q-black 13" should read --- 11α- ---.  Column 30, line 63, "dihydroxyprost13" should read --- dihydroxyprost-13 ---.  Column 36, line 32, "9B" should read --- 9β ---.  Column 44, Claim 1 should read

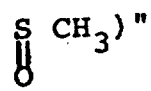

and

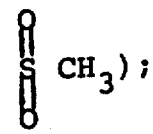

Signed and Sealed this

Twenty-eighth Day of September 1976

[SEAL]

Attest:

RUTH C. MASON
Attesting Officer

C. MARSHALL DANN
Commissioner of Patents and Trademarks